United States Patent
Tripp et al.

(10) Patent No.: US 11,241,406 B2
(45) Date of Patent: Feb. 8, 2022

(54) COMPOSITIONS AND METHODS FOR ACUTLEY RAISING NITRIC OXIDE LEVELS

(71) Applicant: Nature's Sunshine Products, Inc., Lehi, UT (US)

(72) Inventors: Matthew L. Tripp, Saratoga Springs, UT (US); Clinton J. Dahlberg, Saratoga Springs, UT (US); John G. Babish, Brooktondale, NY (US); Mohan Kaadige, Salt Lake City, UT (US); Wei Gao, Lehi, UT (US)

(73) Assignee: Nature's Sunshine Products, Inc., Lehi, UT (US)

( * ) Notice: Subject to any disclaimer, the term of this patent is extended or adjusted under 35 U.S.C. 154(b) by 0 days.

(21) Appl. No.: 15/756,548

(22) PCT Filed: Aug. 28, 2016

(86) PCT No.: PCT/US2016/049306
§ 371 (c)(1),
(2) Date: Feb. 28, 2018

(87) PCT Pub. No.: WO2017/040421
PCT Pub. Date: Mar. 9, 2017

(65) Prior Publication Data
US 2018/0263944 A1    Sep. 20, 2018

Related U.S. Application Data

(60) Provisional application No. 62/211,673, filed on Aug. 28, 2015.

(51) Int. Cl.
*A61K 36/42* (2006.01)
*A61K 31/198* (2006.01)
(Continued)

(52) U.S. Cl.
CPC ............ *A61K 31/198* (2013.01); *A61K 31/51* (2013.01); *A61K 31/555* (2013.01);
(Continued)

(58) Field of Classification Search
CPC ...................................................... A61K 36/42
See application file for complete search history.

(56) References Cited

U.S. PATENT DOCUMENTS 6,706,756 B1 *  3/2004  Fitzpatrick ............. A61K 31/35
                                                                            514/456
7,777,074 B2    8/2010  Kramer et al.
(Continued)

FOREIGN PATENT DOCUMENTS

WO    WO 9959433 A1    11/1999
WO    WO 2004100896 A2    11/2004
(Continued)

OTHER PUBLICATIONS

Anonymous; "ProArgi9Plus Nigeria: ProArgi 9 Plus Site;" proargi9plusng.blogspot.com; (Jun. 17, 2015); 4 pages; [retrieved Jun. 25, 2019]; Retrieved from <URL: http://proargi9plusng.blogspot.com/2015/06/proargi-9-plus-site.html>.
(Continued)

*Primary Examiner* — Rosanne Kosson
(74) *Attorney, Agent, or Firm* — Thorpe North & Western, LLP; David W. Osborne

(57) ABSTRACT

Disclosed herein are compositions and methods for acutely raising nitric oxide levels in a subject. In one example, the composition can include, an effective amount of a NOS dependent source of nitric oxide; an effective amount of a NOS independent source of nitric oxide; and an effective amount of a myeloperoxidase inhibitor; wherein the composition acutely raises nitric oxide levels in a subject above a level provided by the available sources of nitric oxide in
(Continued)

the subject prior to administration of the composition. Further presented is a method of treating a subject for a condition or disorder that is response to nitric oxide therapy, including: acutely raising nitric oxide levels in a subject by simultaneously increasing biosynthesis of nitric oxide, increasing nitrate/nitrite levels, and inhibiting myeloperoxidase activity.

27 Claims, 8 Drawing Sheets

(51) Int. Cl.
| | |
|---|---|
| *A61K 36/87* | (2006.01) |
| *A61K 36/82* | (2006.01) |
| *A61K 36/63* | (2006.01) |
| *A61K 36/185* | (2006.01) |
| *A61K 31/51* | (2006.01) |
| *A61K 31/555* | (2006.01) |
| *A61K 36/534* | (2006.01) |
| *A61K 36/61* | (2006.01) |

(52) U.S. Cl.
CPC .......... *A61K 36/185* (2013.01); *A61K 36/42* (2013.01); *A61K 36/534* (2013.01); *A61K 36/61* (2013.01); *A61K 36/63* (2013.01); *A61K 36/82* (2013.01); *A61K 36/87* (2013.01)

(56) References Cited

U.S. PATENT DOCUMENTS

| | | | |
|---|---|---|---|
| 8,034,836 | B2 | 10/2011 | Kramer et al. |
| 8,048,921 | B2 | 11/2011 | Kramer et al. |
| 8,173,837 | B1 | 5/2012 | Fish |
| 8,178,572 | B2 | 5/2012 | Kramer et al. |
| 8,183,288 | B2 | 5/2012 | Kramer et al. |
| 8,455,531 | B2 | 6/2013 | Kramer et al. |
| 8,466,187 | B2 | 6/2013 | Kramer et al. |
| 8,569,368 | B2 | 10/2013 | Kramer et al. |
| 8,569,369 | B2 | 10/2013 | Kramer et al. |
| 8,952,045 | B1 | 2/2015 | Kramer et al. |
| 8,952,046 | B1 | 2/2015 | Kramer et al. |
| 8,952,047 | B1 | 2/2015 | Kramer et al. |
| 8,957,100 | B1 | 2/2015 | Kramer et al. |
| 8,957,101 | B1 | 2/2015 | Kramer et al. |
| 9,180,140 | B2 | 11/2015 | Lundberg et al. |
| 10,406,118 | B2 | 9/2019 | Lundberg et al. |
| 10,426,750 | B1 | 10/2019 | Kramer et al. |
| 10,426,792 | B1 | 10/2019 | Kramer et al. |
| 10,435,356 | B1 | 10/2019 | Kramer et al. |
| 10,472,322 | B1 | 11/2019 | Kramer et al. |
| 10,555,968 | B2 | 2/2020 | Lundberg et al. |
| 2003/0152656 | A1 | 8/2003 | Pinnell et al. |
| 2006/0115555 | A1 | 6/2006 | Foulger et al. |
| 2010/0227925 | A1 | 9/2010 | Chatfield |
| 2012/0129818 | A1 | 5/2012 | Rajagopal |
| 2013/0071371 | A1 | 3/2013 | Bryan et al. |
| 2015/0065943 | A1* | 3/2015 | DeBow .............. A61K 33/00 604/20 |
| 2019/0125784 | A1 | 5/2019 | Lundberg et al. |
| 2019/0183924 | A1 | 6/2019 | Lundberg et al. |
| 2019/0192554 | A1 | 6/2019 | Lundberg et al. |

FOREIGN PATENT DOCUMENTS

| | | |
|---|---|---|
| WO | 2008105730 | 9/2008 |
| WO | 2008105731 | 9/2008 |
| WO | WO 2014/083438 A2 | 6/2014 |

OTHER PUBLICATIONS

Davidson; "Roasted Salmon with Apple Fennel Salad over Garlicky Kale;" Lexi's Clean Kitchen; (Jan. 15, 2015); 45 pages; [retrieved on Apr. 8, 2019]; Retrieved from <URL: https://lexiscleankitchen.com>.
Delgado Protocol for Health; "Stay Young AM Tablets;" Amazon.com; (Dec. 20, 2012); 6 pages; [retrieved Jun. 2, 2019]; Retrieved from <URL: https://www.amazon.com/Stay-Young-Anti-Aging-Telomeres-Supplement/dp/B006STF9SK>.
GNPD, Mintel; "All-In-One Nutrient Formula Dietary Supplement;" Swanson Health Products; (Sep. 2011); 8 pages; Database Accession No. 1631948.
GNPD, Mintel; "Liquid Dietary Supplement;" Nature's Plus; (May 2010); 6 pages; Database Accession No. 1319372.
Sobon; "Sweet Watermelon, Apple & Carrot Juice;" Vegan Yack Attack!; (Jun. 23, 2014); 6 pages; [retrieved on Apr. 8, 2019]; Retrieved from <URL: http://www.veganyackattack.com >.
Zelman; "The Truth About Beet Juice;" WebMD; (Apr. 5, 2014); 2 pages; [retrieved on Feb. 7, 2019]; Retrieved from <URL: https://www.webmd.com/food-recipes/features/truth-about-beetroot >.
Extended European Search Report dated Mar. 6, 2019, in EP Application No. 16842766.4, filed Aug. 29, 2016; 12 pages.
Bachoual et al.; "An Aqueous Pomegranate Peel Extract Inhibits Neutrophil Myeloperoxidase in Vitro and Attenuates Lung Inflammation in Mice." Food and Chemical Toxicology; Elsevier; Jun. 2011; vol. 49, Issue 6; pp. 1224-1228.
Mohamed.; "Attenuation of Nano-Tio$_2$ Induced Genotoxicity, Mutagenicity and Apoptosis by Chlorophyllin in Mice Cardiac Cells." International Journal of Science and Research; Jun. 2014; vol. 3, Issue 6; pp. 2625-2636.
Nichols et al.; "Skin Photoprotection by Natural Polyphenols: Anti-Inflammatory, Anti-Oxidant and DNA Repair Mechanisms." Arch Dermatol Res; Springer; Mar. 2010; vol. 302, Issue 2; pp. 71-83.
PCT Application No. PCT/US16/49306 Filing date Aug. 29, 2016, Matthew L. Tripp International Search Report, dated Feb. 7, 2017, 18 pages.
Tong et al.; "Fe-Chlorophyllin Promotes the Growth of Wheat Roots Associated with Nitric Oxide Generation." International Journal of Molecular Sciences; Dec. 17, 2010; vol. 11, Issue 12; pp. 5246-5255.
Hongmei et al.; "The Relationship Between Serum Peroxidase and Nitric Oxide and Early-Onset Coronary Three-Vessel Disease;" Shaanxi Medical Journal; (2012); pp. 964-966; vol. 41, Issue 8.
Lidder et al.; "Vascular Effects of Dietary Nitrate (as found in green leafy vegetables and beetroot) via the Nitrate-Nitrite-Nitric Oxide Pathway;" British Journal of Clinical Pharmacology; (2012); pp. 677-696; vol. 75, No. 3; <doi: 10.1111/j.1365-2125.2012.04420.x >.
Lijun; "Research Summary of Grape Polyphenols;" Strait Pharmaceutical Journal; (2009); pp. 103-105; vol. 21, No. 6. [No English translation available].

* cited by examiner

Values are means ± 95% confidence intervals for n=5 and n=4 observations, respectively, for F1 and F2

Values are relative NO2 concentrations from a double of each Formula within a single individual

COMPOSITIONS AND METHODS FOR ACUTLEY RAISING NITRIC OXIDE LEVELS

PRIORITY DATA

This application claims priority benefit to U.S. Provisional Application Ser. No. 62/211,673, filed on Aug. 28, 2015 which is herein incorporated by reference.

BACKGROUND

Nitric oxide influences a number of metabolic pathways and plays a role in vascular signal transduction, neuronal signal transduction, smooth muscle contraction, bioenergetics, platelet adhesion, platelet aggregation, immunity, and cell death. Reduced bioavailable levels of nitric oxide are implicated in numerous conditions and disorders. Nitric oxide plays a key role in the functioning of the cardiovascular, nervous, pulmonary, gastrointestinal, renal, and immune systems. Formulations and methods that provide an acute increase in bioavailable NO would provide a health benefit.

SUMMARY OF THE INVENTION

The present disclosure relates to compositions and methods for acutely raising nitric oxide levels in a subject. The acute raising of nitric oxide levels can be beneficial to the health of a subject. The compositions can include: an effective amount of a NOS (nitric oxide synthase) dependent source of nitric oxide, an effective amount of a NOS independent source of nitric oxide, and a myeloperoxidase (MPO) inhibitor. When administered to a subject, the composition can acutely raise nitric oxide levels in the subject above the level of nitric oxide that is available in the subject prior to the administration of the composition. The NOS dependent source of NO and the NOS independent source of NO can function to increase NO levels in the subject, see FIG. 3, while the MPO inhibitor can prevent oxidative stress associated with MPO. In one example, the composition can acutely raise the level of nitric oxide in the subject following administration of the composition to an amount that is greater than the amount provided by an equivalent amount of any one of the NOS dependent source of nitric oxide, the NOS independent source of nitric oxide, or the myeloperoxidase inhibitor.

BRIEF DESCRIPTION OF THE DRAWINGS

Features and advantages of the invention will be apparent from the detailed description that follows, and which taken in conjunction with the accompanying figures together illustrate features of the invention. It is understood that the figures merely depict exemplary embodiments and are therefore, not to be considered limiting in scope.

DETAILED DESCRIPTION

Figure 1:
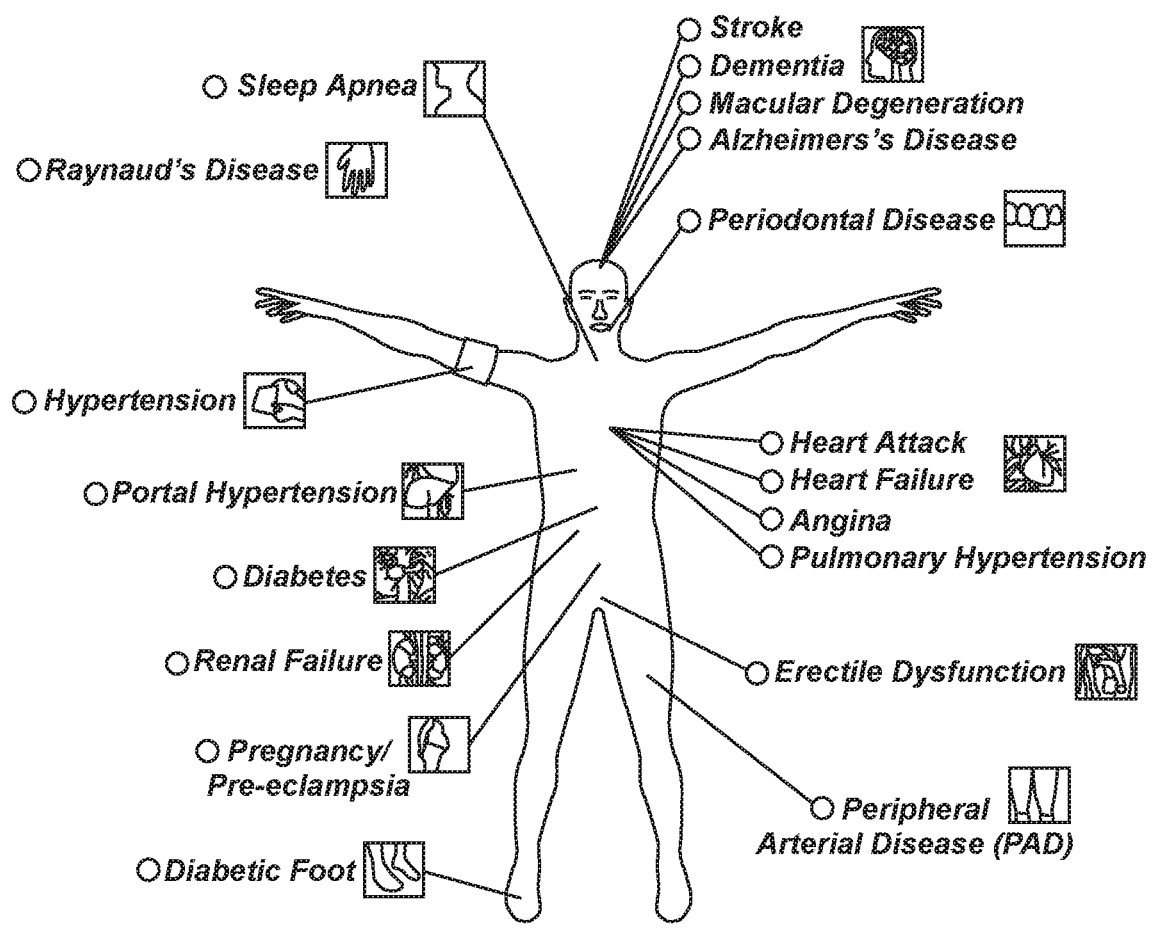
FIG. 1 schematically displays pathophysiologic conditions related to poor eNOS-related NO biosynthesis.

Before invention embodiments are disclosed and described, it is to be understood that no limitation to the particular structures, process steps, or materials disclosed herein is intended, but also includes equivalents thereof as would be recognized by those ordinarily skilled in the relevant arts. It should also be understood that terminology employed herein is used to describe particular examples only and is not intended to be limiting. The same reference numerals in different drawings represent the same element. Numbers provided in flow charts and processes are provided for clarity in illustrating steps and operations and do not necessarily indicate a particular order or sequence. Unless defined otherwise, all technical and scientific terms used herein have the same meaning as commonly understood by one of ordinary skill in the art to which this disclosure belongs. In the specification and the appended claims, the singular forms include plural referents unless the context clearly dictates otherwise.

As used in this written description, the singular forms "a," "an," and "the" specifically also provide express support for plural referents, unless the content clearly dictates otherwise. For example, "an excipient" provides support for one or more excipients.

The term "about" is used herein refers to a degree of deviation. It means approximately, in the region of, roughly, or around. When the term "about" is used in conjunction with a numerical range, it modifies that range by extending the boundaries above and below the numerical values set forth. It is understood that support in this specification for numerical values used in connection with the term "about" is also provided for the exact numerical value itself as though "about" were not used.

As used herein "acute" refers to obtaining the desired effect within a set, or specifically intended, amount of time. In one example, acute refers to an increase or decrease in the concentration, production, secretion, biosynthesis, and/or bioavailability occurring within 30-120 minutes post dosing and lasting for up to 8 hours.

"Bergamot" refers to bergamot orange (*Citrus bergamia* Risso). This citrus species, grows abundantly in the Calabria region of southern Italy, and has been used in Calabrian folk medicine to treat cardiovascular ailments for centuries. Bergamot comprises two 3-hydroxymethylglutaryl (HMG)

derivatives of naturally occurring flavonoid glycosides brutieridin and melitidin. These glycosides are the HMG derivatives of glucosylated hesperetin and naringenin, respectively, and have a structural similarity to the commercially available HMG-CoA reductase inhibitors known as the statins. As used herein bergamot can be used interchangeably to refer to the fruit and/or the extract.

As used herein "cardiometabolic-associated pathologies" or "cardiometabolic risk factors" refers to any condition that increases the risk of those pathologies associated with cardiovascular dysfunction. This generally results from a combination of decreasing the localized production of NO and increasing MPO activity at the same site. A non-limiting example of such pathologies, include: angina, arterial plaque buildup, deep vein thrombosis, dementia, diabetes (types, 1, 2, and 3), diabetic foot disorders, elevated glucose, insulin or HOMA score, elevated hs-CRP (levels greater than 1.0 μmol/L), elevated myeloperoxidase (levels greater than 350 μmol/L), endothelial dysfunction, erectile dysfunction, fibrinogen levels greater than 370 μmol/L, HDL modification, heart attack, heart failure, hypertension (BP greater than 140/90), lipoprotein-associated phospholipase A2 (Lp-PLA2 levels greater than 200 μmol/L), macular degeneration, monocyte-mediated arterial plaque formation, oxidation of LDL, peridontal disease, peripheral arterial disease, platelet stickiness, portal hypertension, pregnancy/pre-eclampsia, pulmonary hypertension, renal failure, serum low density lipoprotein (LDL) greater than 150 mg/dL, serum triglycerides greater than 150 mg/dL, sleep apnea, smooth muscle cell proliferation, stroke, and vasculitis.

As used herein, chemical compounds or simply "compounds" may be identified either by their chemical structure, chemical name, or common name. In the event that the chemical structure, chemical name, or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers, or diastereomers. Accordingly, the chemical structures depicted herein encompass all possible enantiomers and stereoisomers of the illustrated or identified compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$ etc. Compounds may exist in unsolvated forms as well as solvated forms, including hydrated forms and as N-oxides. In general, compounds may be hydrated, solvated, or N-oxides. Certain compounds may exist in multiple crystalline or amorphous forms. Also contemplated are congeners, analogs, hydrolysis products, metabolites, and precursor or prodrugs of the compound. In general, all physical forms are equivalent for the uses contemplated herein and are intended to be within the scope of the present disclosure.

Concentrations, amounts, and other numerical data may be expressed or presented herein in a range format. It is to be understood that such a range format is used merely for convenience and brevity and thus should be interpreted flexibly to include not only the numerical values explicitly recited as the limits or endpoints of the range, but also to include all the individual numerical values and/or sub-ranges encompassed within that range as if each numerical value (including fractions) and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 2.6, 3, 3.8, and 4 and sub-ranges such as from 1-3, from 2-4, and from 3-5, etc., as well as 1, 2, 3, 4, and 5, individually.

As used herein a "concentrate" refers to an extract of a source that contains at least the same amount of active fractions, compounds, or other constituents, in a smaller volume than in the source itself. In one example, a "concentrate" may be a dried powder derived from a component that does not include the use of any solvents during the concentration process.

Comparative terms such as "more effectively," "greater than," "improved," "enhanced," and like terms can be used to state a result achieved or property present in a formulation or process that has a measurably better or more positive outcome than the thing to which comparison is made. In some instances comparison may be made to the prior art.

As used herein, "comprises," "comprising," "containing," and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term in the written description, like "comprising" or "including," it is understood that direct support should be afforded also to "consisting essentially of" language, as well as, "consisting of" language as if stated explicitly and vice versa.

As used herein, a "derivative" is a compound obtained from a source compound an analog, homolog tautomeric form, stereoisomer, polymorph, hydrate, pharmaceutically acceptable salt or pharmaceutically acceptable solvate thereof, by a simple chemical process converting one or more functional groups, by means of oxidation, hydrogenation, alkylation, esterification, halogenation and the like. The term "analog" refers to a compound having a structure similar to that of another one, but differing from it with respect to a certain component. The compound may differ in one or more atoms, functional groups, or substructures, which may be replaced with other atoms, groups, or substructures. In one aspect, such structures possess at least the same or a similar therapeutic efficacy for a given indication. The term "tautomer" or "tautomeric form" refers to structural isomers of different energies which are interconvertible via a low energy barrier. The term "stereoisomer" refers to one of a set of isomers whose molecules have the same number and kind of atoms bonded to each other, but which differ in the way these atoms are arranged in space. The term "polymorph" refers to crystallographically distinct forms of a substance. In addition, an agent can be said to be "derived" from a source containing many compounds or agents, such as a plant, fungus, bacteria, or other organism. In this context, the agent can be described or otherwise referred to in terms of its source, rather than by its own properties, characteristics, name, or attributes per se. For example, an extract obtained from a plant may be described as "derived" from the plant.

The term "dosage unit" is understood to mean a unitary, i.e. a single dose which is capable of being administered to a subject or patient, and that may be readily handled and packed, remaining as a physically and chemically stable unit dose comprising either the active ingredient as such or a mixture of it with solid or liquid pharmaceutical vehicle materials.

The phrase "effective amount," "therapeutically effective amount," or "therapeutically effective rate(s)" of an active ingredient refers to a non-toxic, but sufficient amount or delivery rates of the active ingredient, to achieve therapeutic results in treating a disease or condition for which the drug is being delivered. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

The term "extract" refers to those substances prepared using a solvent, e.g., ethanol, water, steam, superheated water, methanol, hexane, chloroform liquid, liquid $CO_2$, liquid $N_2$, propane, supercritical $CO_2$, or any combination thereof. Extracts, as used herein, can refer to an extract in a liquid form, or can refer to a product obtained from further processing of the liquid form, such as a dried powder or other solid form. Extracts may take many forms including but not limited to: solid, liquid, particulate, chopped, distillate, etc. and may be performed by any number of procedures or protocols, such as chopping, grinding, pulverizing, boiling, steaming, soaking, steeping, infusing, applying a gas, etc., and may employ any suitable reagents, such as water, alcohol, steam, or other organic materials. Extracts typically have a given purity percentage and can be relatively to highly pure. In some embodiments, extracts can be phytoextracts made from specific parts of a source, such as the skin, pulp, leaves, flowers, fruits of a plant etc., or can be made from the whole source. In some aspects an extract may include one or more active fractions or active agents. In some extracts, maltodextrin can be added as a carrier. In some aspects, the purity of an extract can be controlled by, or be a function of the extraction process or protocol.

As used herein, "formulation" and "composition" can be used interchangeably and refer to a combination of at least two ingredients. In some embodiments, at least one ingredient may be an active agent or otherwise have properties that exert physiologic activity when administered to a subject.

Formulation or compositional ingredients included or recited herein are to be presumed to be in wt % unless specifically stated otherwise. In addition, ingredient amounts presented in the form of ratios are to be presumed to be in wt % (e.g. % w/w) ratios. As such, a composition containing four ingredients at a 1:1:1:1 ratio would indicate that each ingredient is present in an amount of 25 wt %. Accordingly, in some aspects, the amount of an ingredient in a composition or formulation in terms of wt % can be derived from a numerical ratio value.

As used herein, an "increase" or a "decrease" in concentrations or levels means a change of at least 5%.

As used herein, "inhibit," "inhibiting," "inhibition," and like terms refer to the act of reducing, minimizing, stopping or arresting a function, role, or activity. For example, these terms can mean reducing, minimizing, stopping, arresting, or effectively reducing, minimizing, stopping, or arresting myeloperoxidase activity in a subject.

As used herein, "Leaky Gut Syndrome (LGS)" is an increase in permeability of the intestinal mucosa to luminal macromolecules, antigens and toxins associated with inflammatory degenerative and/or atrophic mucosal damage. LGS can lead to any number of seemingly unrelated symptoms affecting every organ system in the body. LGS has also been linked with having a causative role in a large number of distinct illnesses. Many of these are autoimmune diseases, which means the immune system attacks the body's own cells. LGS plays a role in these types of illness because it increases immune reactions to food particles and then cross reactivity may occur meaning that the immune system attacks body tissues that are chemically similar to the foods to which it has become sensitized. A sampling of the many diseases in which leaky gut syndrome may have a role includes: rheumatoid arthritis, osteoarthritis, asthma, multiple sclerosis, vasculitis, Crohn's Disease, colitis, Addison's disease, lupus, thyroiditis, chronic fatigue syndrome, and fibromyalgia.

As used herein, "linear inhibitory effect" or "dose-response" refers to a linear decrease in secretion or biosynthesis resulting from all concentrations of the inhibiting material over a dose-response curve. For example, inhibition at low concentrations followed by a failure of inhibition or increased secretion at higher concentrations represents a lack of a linear inhibitory effect.

The term "or" is used in the "inclusive" sense of "and/or" and not the "exclusive" sense of "either/or."

As used herein, "pharmaceutically acceptable" refers generally to materials which are suitable for administration to a subject in connection with an active agent or ingredient. For example, a "pharmaceutically acceptable carrier" can be any substance or material that can be suitably combined with an active agent to provide a composition or formulation suitable for administration to a subject. Excipients, diluents, and other ingredients used in or used to prepare a formulation or composition for administration to a subject can be used with such term.

The term "prevent" and its variants refer to prophylaxis against a particular undesirable physiological condition. The prophylaxis may be partial or complete. Partial prophylaxis may result in the delayed onset of a physiological condition. The person skilled in the art will recognize the desirability of delaying onset of a physiological condition, and will know to administer the compositions of the invention to subjects who are at risk for certain physiological conditions in order to delay the onset of those conditions. For example, the person skilled in the art will recognize that obese subjects are at elevated risk for coronary artery disease. Thus, the person skilled in the art will administer compositions of the invention in order to increase insulin sensitivity in an obese, whereby the onset of diabetes mellitus or dyslipemia may be prevented entirely or delayed.

As used herein, a "subject" refers to an organism that produces nitric oxide and myloperoxidase in the course of its cellular function. In one aspect, a subject can be a mammal. In another aspect, a subject can be a human. In another aspect, the subject can be a domesticated animal or livestock.

As used herein, "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context. Similarly, "substantially free of" or the like refers to the lack of an identified element or agent in a composition. Particularly, elements that are identified as being "substantially free of" are either completely absent from the composition, or are included only in amounts which are small enough so as to have no measurable effect on the composition.

The terms "treat," "treating," or "treatment" as used herein and as well understood in the art, mean an approach for obtaining beneficial or desired results, including without limitation clinical results in a subject being treated. Beneficial or desired results can include, but are not limited to, alleviation or amelioration of one or more signs or symptoms of a condition, diminishment of extent of disease, stabilizing (i.e. not worsening) the state of a disease or condition, delaying or slowing of disease progression, amelioration or palliation of the disease state, diminishment of the reoccurrence of disease, and remission (whether partial or total), whether detectable or undetectable. "Treat," "treating" and "treatment" can also mean prolonging survival as compared to expected survival if not receiving treatment and can be prophylactic. Such prophylactic treatment can also be referred to as prevention or prophylaxis of a disease or condition. The prophylaxis may be partial or complete. Partial prophylaxis may result in the delayed onset of a physiological condition.

As used herein, the term "solvent" refers to a liquid of gaseous, aqueous, or organic nature possessing the necessary characteristics to extract solid material from a plant product. Examples of solvents would include, but not limited to, water, steam, superheated water, methanol, ethanol, ethyl acetate, hexane, chloroform, liquid $CO_2$, liquid $N_2$, propane, or any combinations of such materials.

As used herein, "synergistic" means more than the additive effect of the individual components against a mechanism of action. For example if F1 produces response X, F2 produces response Y, then the combination of F1+F2>X+Y. In some situations F2 produces no response and the value for Y is equal to zero.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Any steps recited in any method or process claims may be executed in any order and are not limited to the order presented in the claims unless otherwise stated.

Nitric Oxide (NO) is a free radical, actively produced in the human body. NO plays a role in the normal functioning of the cardiovascular, nervous, pulmonary, gastrointestinal, renal, and immune systems. See Table 1.

TABLE 1

Exemplary Established Functions of Nitric Oxide

| System | Function |
|---|---|
| Cardiovascular | Controls vascular tone. |
| | Relaxes vascular smooth muscles and reduces blood pressure. |
| | Dilates vessels and relieves the pain of angina. |
| | Inhibits the aggregation of platelets within the vessels and prevents thrombotic events. |
| | Controls vascular tone. |
| | Relaxes vascular smooth muscles and reduces blood pressure. |
| | Dilates vessels and relieves the pain of angina. |
| | Inhibits the aggregation of platelets within the vessels and prevents thrombotic events. |
| Nervous | Acts as a neurotransmitter, including in the autonomic nervous system. |
| | Increases cerebral blood flow and oxygenation to the brain. |
| | Important mediator in penile erection during sexual arousal. |
| Pulmonary | Dilates pulmonary vessels. |
| | Benefits Adult Respiratory Distress Syndrome, pulmonary hypertension and Chronic Obstructive Airway Disease. |
| | Produced in abnormal amounts in inflammatory lung conditions. |
| | Concentration of NO in exhaled air can be taken as a marker of airway inflammation. |
| Gastrointestinal | Regulates the relaxation of smooth muscles. |
| | Controls peristalsis and the function of sphincters. |
| Renal | Increases blood flow to the kidney due to its vasodilatory effect. |
| | Increases the glomerular filtration rate and the production of urine. |
| Immune | Modulates T cell-mediated immune response. |

Figure 2:
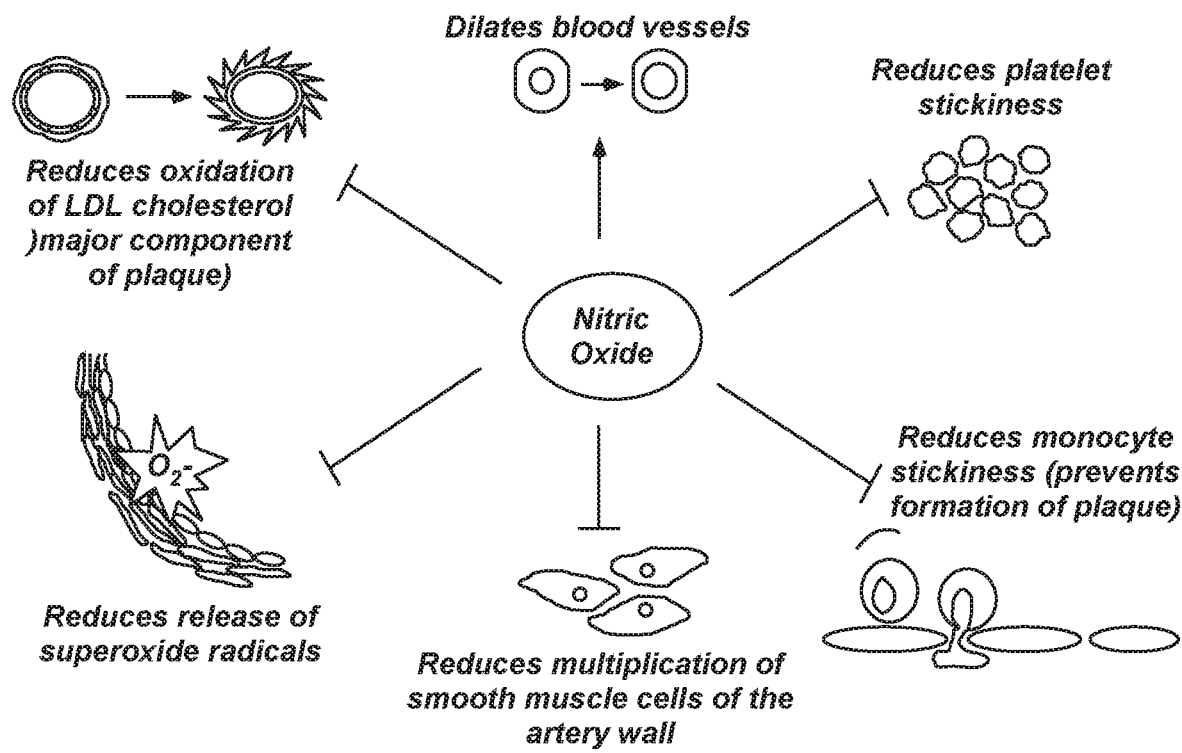
FIG. 2 schematically displays the positive effects of NO in peripheral vascular diseases related to cardiometaboic risk factors.

Defective control of nitric oxide levels can play a role in numerous pathologies as shown in FIG. 1. These pathologies include: angina, Alzheimer's disease, dementia, diabetic foot, diabetes, erectile dysfunction, heart attack, heart failure, hypertension, portal hypertension, peripheral arterial disease, pulmonary hypertension, macular degeneration, periodontal disease, pregnancy related pre-eclampsia, Raynaud's disease, renal failure, sleep apnea, and stroke. With respect to cardiovascular pathophysiology, nitric oxide can activate soluble guanylate cyclase (sGC)-cGMP signal transduction pathways which can mediate various beneficial physiological effects in the cardiovascular system including vasodilation, inhibition of platelet aggregation, reduction of monocyte "stickiness" to prevent formation of plaque, reduction of smooth muscle cell proliferation, inhibition of superoxide radical formation, and reduction of LDL oxidation. See FIG. 2.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

Figure 3:
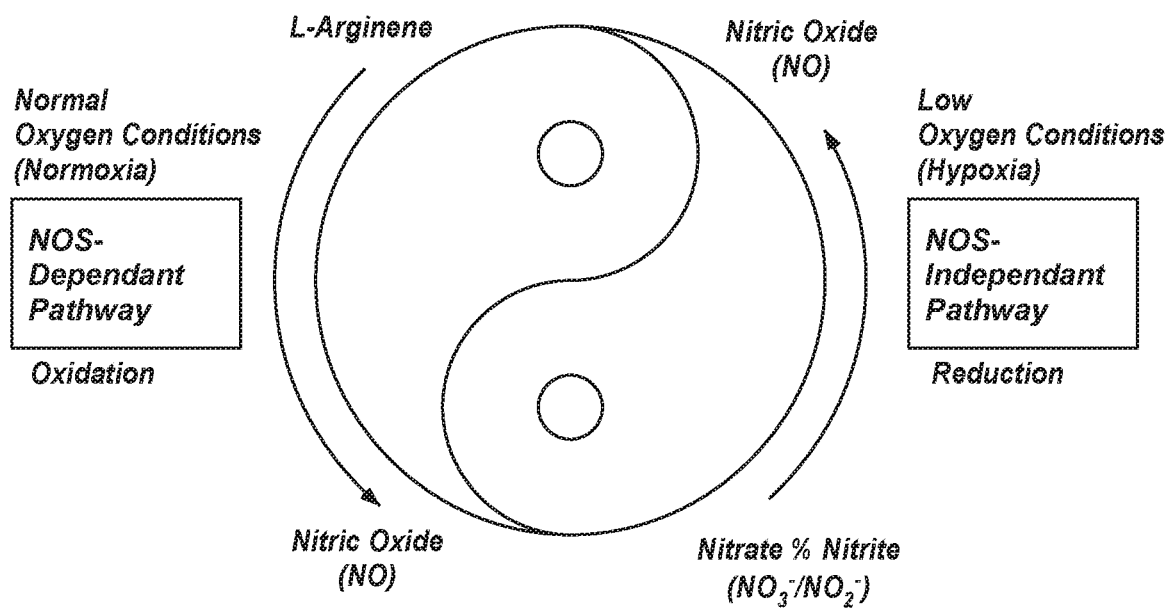
FIG. 3 schematically displays NO production by NOS-dependent (L-arginine) and NOS independent (NO3/NO2) pathways.

The present disclosure relates to compositions and methods for acutely raising nitric oxide levels in a subject. The acute raising of nitric oxide levels can be beneficial to the health of a subject. The compositions can include: an effective amount of a NOS (nitric oxide synthase) dependent source of nitric oxide, an effective amount of a NOS independent source of nitric oxide, and a myeloperoxidase (MPO) inhibitor. When administered to a subject, the composition can acutely raise nitric oxide levels in the subject above the level of nitric oxide that is available in the subject prior to the administration of the composition. The NOS dependent source of NO and the NOS independent source of NO can function to increase NO levels in the subject, see FIG. 3, while the MPO inhibitor can prevent oxidative stress associated with MPO. In one example, the composition can acutely raise the level of nitric oxide in the subject following administration of the composition to an amount that is greater than the amount provided by an equivalent amount of any one of the NOS dependent source of nitric oxide, the NOS independent source of nitric oxide, or the myeloperoxidase inhibitor.

Figure 4:
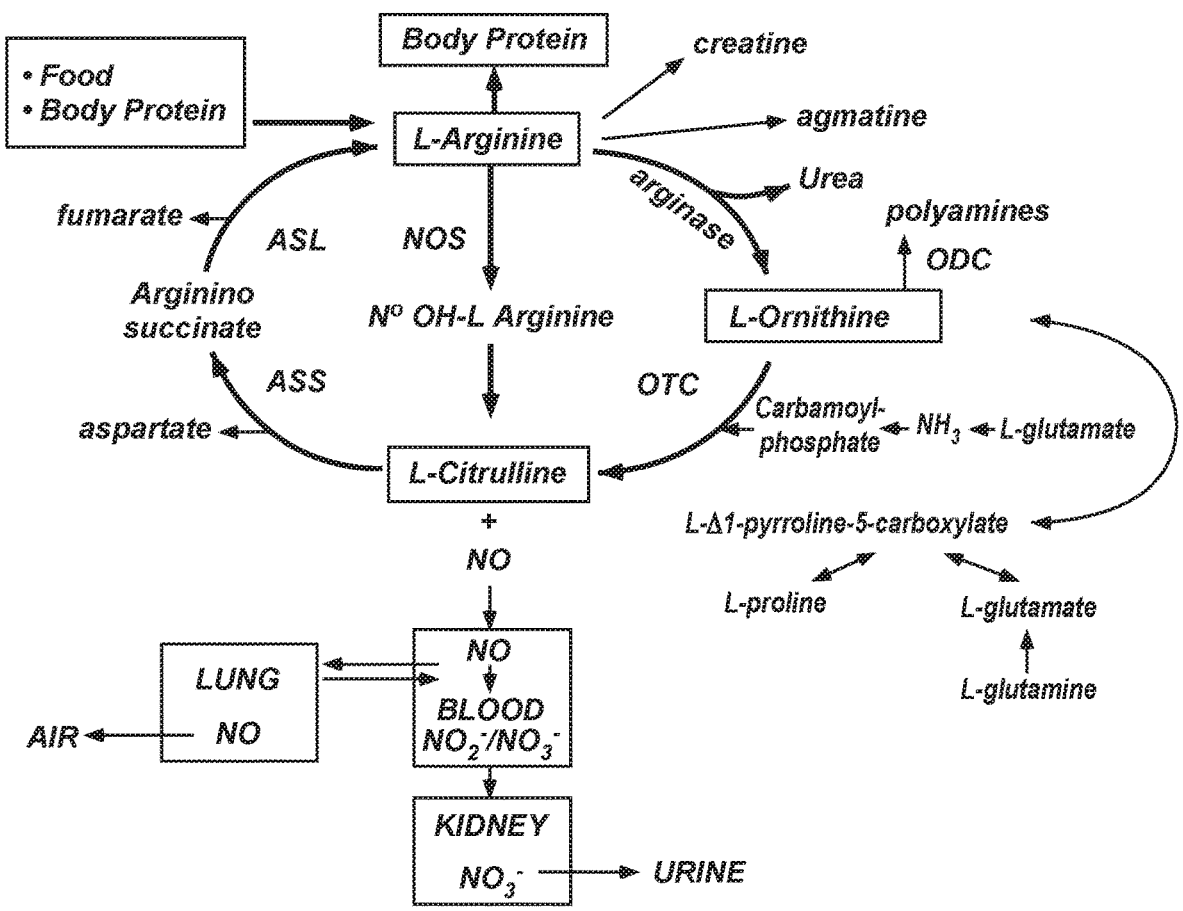
FIG. 4 schematically displays the nitric oxide cycle.

NOS dependent sources of nitric oxide (NO) can include compounds that can be catalyzed by NOS to produce NO. The nitric oxide cycle is shown in FIG. 4. As shown in FIG. 4 L-arginine, L-citrulline, and ornithine are all components in the nitric oxide cycle. Nitric oxide produced from NOS dependent sources have a half-life of approximately one second and are quickly oxidized to $NO_3/NO_2$ or react with thiols or amines in the body. In one example, the NOS dependent source of nitric oxide in the composition, can include L-arginine, L-citrulline, ornithine, or a combination thereof. In one example, the NOS dependent sources of nitric oxide can comprise from about 40 wt % to about 98 wt % of the composition. In another example, the NOS dependent sources of nitric oxide can comprise from 0.01 wt % to 15 wt % of the composition.

In another example, the NOS dependent source of nitric oxide comprises L-arginine. In one example, the L-arginine in the composition can range from about 1 wt % to about 80 wt %. In another example, the L-arginine in the composition can range from about 0.5 wt % to about 90 wt %. In yet another example, the L-arginine in the composition can range from about 0.25 wt % to about 95 wt %. In a further example, the L-arginine can be in the composition from about 0.125 wt % to about 99 wt %. In yet a further example, the L-arginine can be in the composition from about 40 wt % to about 95 wt %. In another example, the L-arginine can be in the composition from 0 wt % to about 10 wt %.

In another example, the NOS dependent source of nitric oxide can include L-citrulline. In one example, the L-citrulline can be present in the composition from about 1 wt % to about 80 wt %. In another example, the L-citrulline can be present in the composition from about 0.5 wt % to about 90 wt %. In yet another example, the L-citrulline can be present in the composition from about 0.25 wt % to about 95 wt %. In a further example, the L-citrulline can be present in the composition from about 0.125 wt % to about 99 wt %. In yet a further example, the L-citrulline can be present in the composition from about 0.1 wt % to about 5 wt %. In yet another example, the L-citrulline can be present from about 0.5 wt % to about 2.5 wt %.

In some examples, the source of the L-citrulline can be a watermelon extract. In one example, the watermelon extract can include about 20 wt % citrulline. In another example, the watermelon extract can include about 10 wt % citrulline, about 15 wt % citrulline, about 25 wt % citrulline, about 30 wt % citrulline, about 40 wt % citrulline, or about 50 wt % citrulline.

In yet another example, the NOS dependent source of nitric oxide can include L-arginine and L-citrulline. In one example, the L-arginine can range from about 1 wt % to about 80 wt % and the L-citrulline can range from about 1 wt % to about 80 wt %. In another example, the L-arginine can range from about 0.5 wt % to about 90 wt % in and the L-citrulline can range from about 0.5 wt % to about 90 wt %. In yet another example, the L-arginine can range from about 0.25 wt % to about 95 wt % and the L-citrulline can range from about 0.25 wt % to about 95 wt %. In yet a further example, the L-arginine can range from about 40 wt % to about 95 wt % and the L-citrulline can range from about 0.1 wt % to about 5 wt %.

The ratio of the weight percentage of L-arginine and L-citrulline can also vary. In one example, the L-arginine and L-citrulline can be present in the composition at a weight percent concentration ranging from about 1:5 to about 5:1, respectively. In another example, the L-arginine and L-citrulline can be present in the composition at a weight percent concentration ranging from about 1:1 to about 5:1, respectively. In yet another example, the L-arginine and L-citrulline can be present in the composition at a weight percent concentration of about 2:1, respectively.

Figure 5:
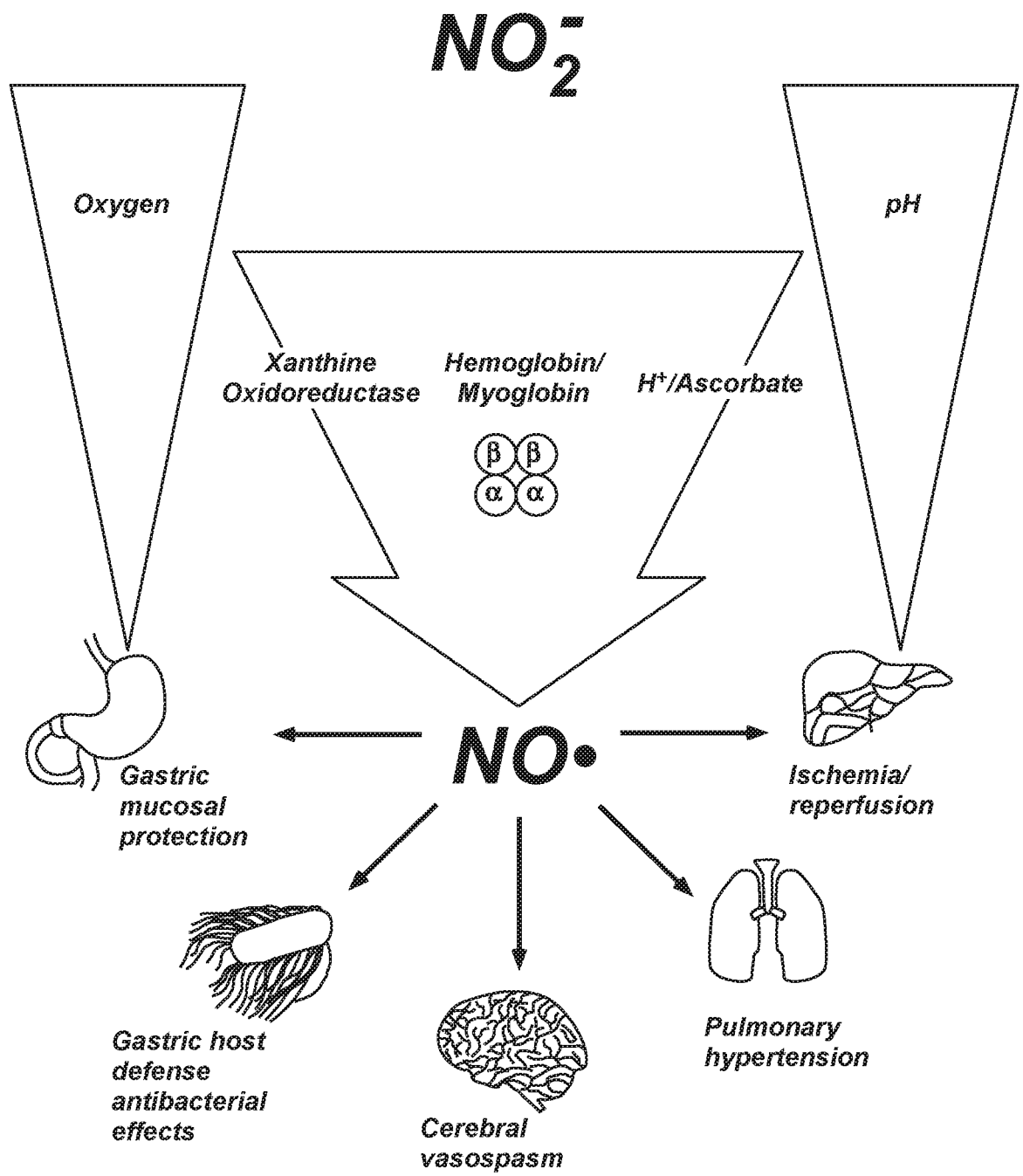
FIG. 5 schematically displays the pathways for NO2 reduction to NO at specific sites of action addressing system pathologies.

Turing now to the NOS independent source of nitric oxide. NOS independent sources of nitric oxide, can include dietary sources of nitrates/nitrites. $NO_3$ (nitrate) can be reduced by facultative anaerobic bacteria on the dorsal surface of the tongue to nitrite ($NO_2$). The $NO_2$ can then be enzymatically reduced to NO. See FIG. 5. The bioavailability of dietary $NO_3$ is 100%. Orally consumed $NO_3$ can reach peak plasma concentration in about 1 hour and has a half-life in plasma of about 5 hours.

In one example, the NOS independent source of nitric oxide can include a member selected from the group consisting of beet root extract, vitamin B1, collard green extract, nut powders, spinach extract, broccoli extract, lettuce extract, celery, kale, watercress, carrot, arugula, mustard greens, or a combination thereof.

In one example, the NOS dependent source of nitric oxide can be in the composition at a range from about 1 wt % to about 80 wt %. In another example, the NOS dependent source of nitric oxide can be in the composition at a range from about 0.01 wt % to about 90 wt %. In another example, the NOS dependent source of nitric oxide can be present in the composition from about 15 wt % to about 30 wt %.

In one example, the NOS independent source of nitric oxide can include beet root extract, vitamin B1, or a combination thereof. In another example, the NOS independent source of nitric oxide can include the beet root extract and the vitamin B1. In one example, including beet root extract and vitamin B1, the beet root extract can range from about 5 wt % to about 90 wt % and the vitamin B1 can range from about 0.01 wt % to about 80 wt % of the composition. In another example, including beet root extract and vitamin B1, the beet root extract can range from about 1 wt % to about 95 wt % and the vitamin B1 can range from about 0.005 wt % to about 99 wt % of the composition. In yet another example, including beet root extract and vitamin B1, the beet root extract can range from about 0.1 wt % to about 99 wt % and the vitamin B1 can range from about 0.0025 wt % to about 0.995 wt % of the composition. In a further example, the beet root extract can range from about 15 wt % to about 30 wt % and the vitamin B1 can range from about 0.5 wt % to about 5 wt %.

In formulations including beet root extract and vitamin B1, the ratio of these components can also vary. In one example, the beet root extract and vitamin B1 can be present in the composition at a weight percent concentration ratio ranging from about 50:1 to about 10:1, respectively. In another example, the beet root extract and vitamin B1 can be present in the composition at a weight percent concentration ratio ranging from about 100:1 to about 1:1, respectively. In a further example, the beet root extract and vitamin B1 can be present in the composition at a weight percent concentration ratio ranging from about 1,000:1 to about 1:2, respectively.

Figure 6:
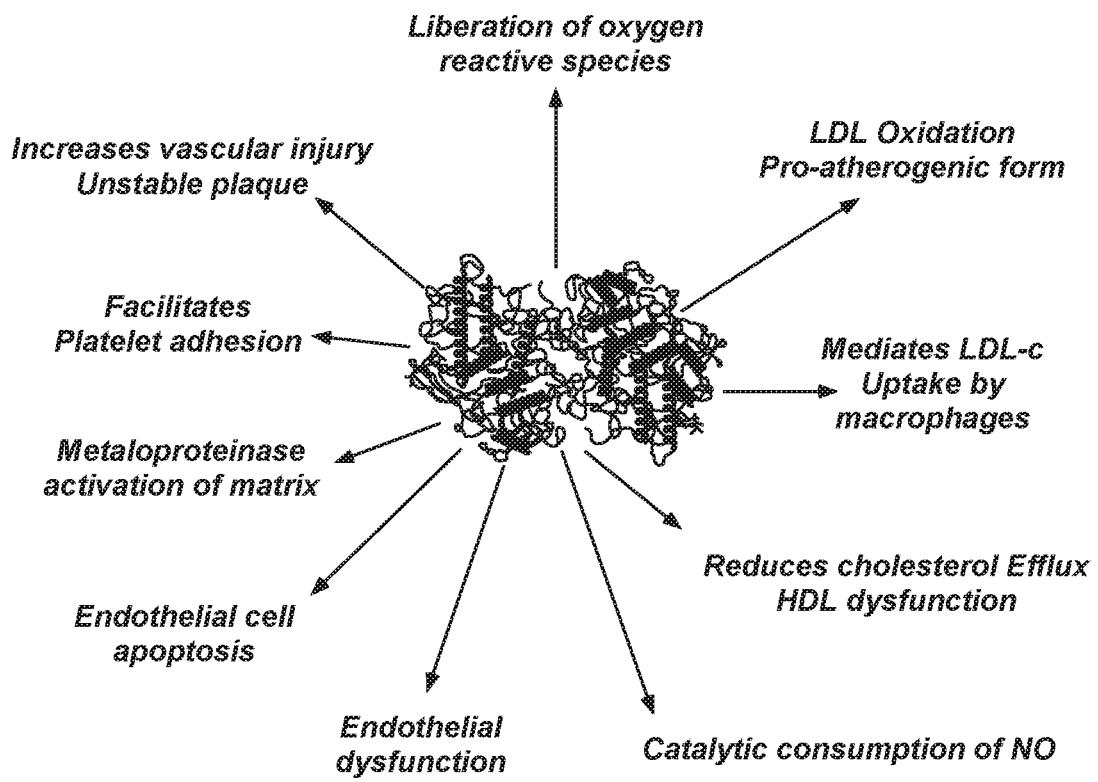
FIG. 6 schematically displays the multiple roles of myeloperoxidase in cardiometabolic pathologies and oxidative stress.
Figure 7:
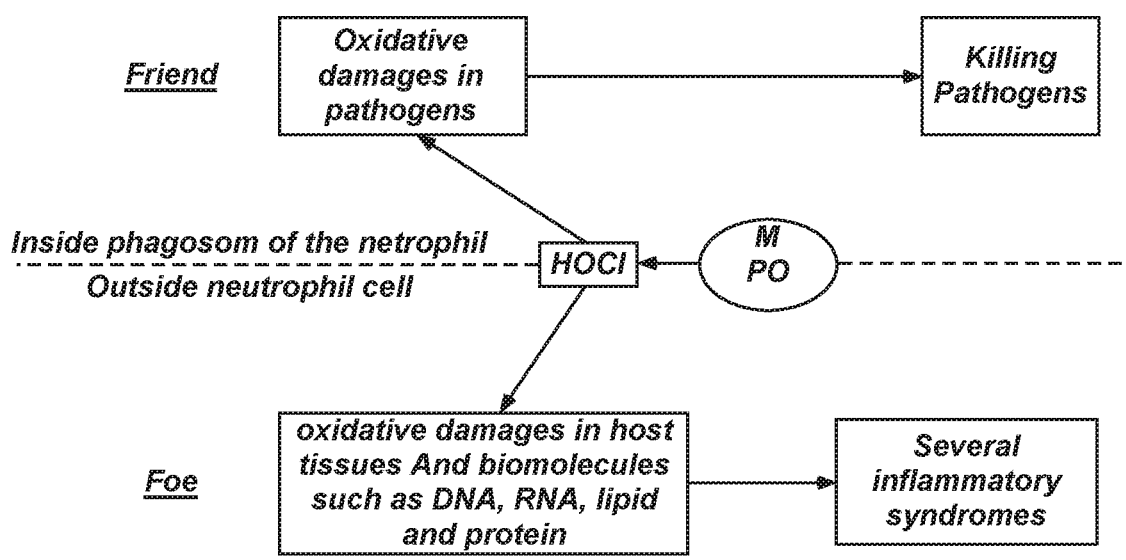
FIG. 7 schematically displays the dual role of myeloperoxidase in acute disease prevention and chronic disease causation.

Turning now to the myeloperoxidase inhibitor. Myeloperoxidase (MPO) is a heme containing enzyme that produces hypochlorous acid (HOCl) as part of the body's defense mechanism on invading organisms. See FIGS. 6 and 7. MPO also exacerbates inflammatory diseases and promotes oxidative stress. Accordingly, MPO inhibitors can be useful in the treatment of conditions and pathologies associated with oxidative stress.

In one example, the myeloperoxidase inhibitor can be pomegranate fruit extract, red grape polyphenols, apple extract, blueberry extract, capsicum extract, grape extract, green tea extract, olive extract, bergamot extract, mangosteen extract, mangosteen fruit, or a combination thereof. In one example, the myeloperoxidase inhibitor can range from about 1 wt % to about 90 wt %. In another example, the myeloperoxidase inhibitor can range from about 0.5 wt % to about 95 wt %. In yet another example, the myeloperoxidase inhibitor can range from about 0.25 wt % to about 99 wt %. In another example, the myeloperoxidase inhibitor can range from about 1 wt % to about 15 wt %. In yet a further example, the myeloperoxidase inhibitor can range from about 3 wt % to about 12 wt %.

In one example, the myeloperoxidase inhibitor can include pomegranate fruit extract, red grape polyphenols, or a combination thereof. In another example, of the composition, the myeloperoxidase inhibitor can include pomegranate fruit extract and red grape polyphenols. In one example, the pomegranate fruit extract can range from about 1 wt % to about 80 wt % and the red grape polyphenols can range from about 1 wt % to about 80 wt % of the composition. In another example, the pomegranate fruit extract can range from about 0.5 wt % to about 90 wt % and the red grape polyphenols can range from about 0.5 wt % to about 90 wt % of the composition. In yet another example, the pomegranate fruit extract can range from about 0.25 wt % to about 95 wt % and the red grape polyphenols can range from about 0.25 wt % to about 95 wt % of the composition. In one example, the pomegranate fruit extract can range from about 0.25 wt % to about 10 wt % and the red grape polyphenols can range from about 0.01 wt % to about 2 wt % of the composition.

In another example, the myeloperoxidase inhibitor can include apple extract, grape extract, green tea extract, and olive extract. In one example, the apple extract, the grape extract, the green tea extract, and the olive extract collectively can range from about 1 wt % to about 80 wt % of the composition. In another example, the apple extract can range from about 0.01 wt % to about 80 wt %, the grape extract can range from about 0.01 wt % to about 80 wt %, the green tea extract can range from about 0.01 wt % to about 80 wt %, and the olive extract can range from about 0.01 wt % to about 80 wt % of the claimed composition. In yet another example, the apple extract can range from about 0.01 wt % to about 5 wt %, the grape extract can range from about 0.01 wt % to about 7 wt %, the green tea extract can range from about 0 wt % to about 1 wt %, and the olive extract can range from about 0 wt % to about 1 wt % of the claimed composition. In another example, the apple extract, the grape extract, the green tea extract, and the green tea leaf extract, are each present in the composition from about 0.01 wt % to about 1 wt %.

In one example, the apple extract can comprise an extract derived from a member selected from the group consisting of *Malus domestica, Malus sieversii, Malus sylvestris, Malus pumila*, and combinations thereof. In one example the apple extract can be derived from the species *Malus pumila*. In one example, the apple extract can be derived from a combination of *Malus domestica* and *Malus pumila*. In some embodiments the apple extract can comprise any or all parts of the apple, including but not limited to the skin, flesh/fruit (exocarp, mesocarp, and/or endocarp), seed, stalk, stem, leaf, or a combination thereof. In one example, the apple extract comprises the skin and fruit of the apple. In some embodiments, the extract can be derived from immature apples. In one embodiment, an extraction solvent can be ethanol.

In one example, the grape extract can comprise a member selected from the group consisting of *Vitis vinifera, Vitis labrusca, Vitis riparia, Vitis rotundifolia, Vitis rupestris, Vitis aestivalis, Vitis mustangensis*, and combinations thereof. In one example, the grape extract can be derived from *Vitis vinifera*. In some embodiments, the grape extract can comprise any or all parts of the grape including but not limited to the skin, flesh/fruit, seed, vascular bundles, vine, leaves, or combination thereof. In one embodiment, the grape extract can be derived from the seeds. In another embodiment, the grape extract can be derived from the skin. In yet another embodiment, the grape extract can be derived from the seeds and skin of the grape. In some embodiments, the grape extract comprises from about 75 wt % to about 95 wt % phenolics on a dry weight basis. In other embodiments, the grape extract can comprise from about 80 wt % to 97 wt % phenolics on a dry weight basis. In one example, the extraction solvent can be ethanol, water, or a mixture thereof.

In one example, the green tea extract can be derived from *Camellia sinensis*. In some embodiments, the green tea extract can comprise any or all parts of the tea including but not limited to the leaf, seed, stem, flower, or combination thereof. In one embodiment, the green tea extract can be derived from the leaves. In another example, the extract solvent can be water, ethanol, ethyl acetate, or combinations thereof.

In one example, the olive extract comprises a subspecies of *Olea europea* selected from the group consisting of the subspecies *europea, cuspidiata, guanchica, cerasiformis, maroccana, laperrinei, cerasiformis*, or a combination thereof. In some embodiments, the olive extract can comprise any or all parts of the olive including but not limited to the leaf, seed, pulp, fruit, stem, or combination thereof. In one embodiment, the olive extract can be derived from the leaves. In another example, the extraction solvent can be an ethanol and water solution.

In some embodiments, the plant or herb to extract ratio can range from about 1 to about 10. In other examples, the raw plant or herb to extract ratio can be from about 2 to about 5, from about 4 to about 7, or from about 8 to about 10.

By way of example, in some embodiments, each extract can be present at a ratio of from about 1 to about 50 times the amount of another extract. In one aspect, the apple extract can be present in the formulation at a ratio of from 1 to 50 times the amount of a grape, green tea, or olive extract. In another aspect, the apple extract can be present in the formulation at a ratio of from about 1 to 25 times the amount of a grape, green tea, or olive extract. In a further aspect, the apple extract in the formulation can be present at a ratio of from 1 to 10 times the amount of a grape, green tea, or olive extract. In an additional aspect, the apple extract can be present in at a ratio of from 1 to 5 times the amount of a grape, green tea, or olive extract. In yet another aspect, the apple extract can be present in the formulation at a ratio of 1 times the amount of a grape, green tea, or olive extract.

Any specific numerical value within the numerical range is included. In fact, each of the apple, grape, green tea, and olive extracts may be present in a ratio of anywhere between 1 to 50 times and 1 times the amount of the other extracts. For example, the amount of apple extract to grape extract to green tea extract to olive extract may in some embodiments be 1-25:1-25:1-25:1-25 respectively. As such, any number given specific ratio that yields a synergistic effect as recited herein can be used, for example 25:1:1:1, 1:25:1:1, 1:1:25:1, or 1:1:1:25. When considered in terms of wt %, this would equate to one ingredient being present in an amount of 89.28 wt % and the other three ingredients being present in amounts of 3.57 wt %. This can be considered either in terms of the formulation as a whole, or in terms of the myeloperoxidase inhibitor in the formulation only. For example, these four extracts, at a 1:1:1:1 ratio would result in a relative amount of each at 25 wt % each (i.e. 100/4=25). In one example, the apple extract, grape extract, green tea extract, and olive extract can be present in the composition at a weight ratio of about 1:1:1:1. In another example, the apple extract, grape extract, green tea extract, and olive extract can be present in the composition at a weight ratio of about 6:1:3:1. In a further example, at least one of the apple extract, the grape extract, the green tea extract, and the olive extract are present in the composition in a different amount.

In one example, the myeloperoxidase inhibitor can further include pomegranate fruit extract. In another example, the myeloperoxidase inhibitor can further include blueberry fruit extract, capsicum fruit extract, and turmeric root extract. In one example, the blueberry extract/concentrate can be obtained from *Vaccinium angustifolium*. In one example the blueberry concentrate can be a dried powder created without the use of a solvent. In one embodiment, it can take about 5 kg, about 8 kg, about 10 kg, or about 12 kg of blueberries to obtain 1 kg of dried powder. In one embodiment, the capsicum extract can be obtained from *Capsicum annuum*. In some embodiments, capsicum extract can be derived from powdered dried ripe fruits. In one example the turmeric extract can be obtained from *Curcuma longa*. In some embodiments, the turmeric extract can be derived from a turmeric powder. In on embodiment, the turmeric powder can have from about 1 to about 10% curcuminoids, from about 3 to about 5% curcuminoids, from about 2% to about 8% curcuminoids, or from about 4% to about 12% curcuminoids.

The amount of the myeloperoxidase inhibitor can also vary. In one example, the blueberry fruit extract can range from about 0.01 wt % to about 80 wt %, the capsicum fruit extract can range from about 0.01 wt % to about 80 wt %, and the turmeric root extract can range from about 0.01 wt % to about 80 wt % of the composition. In another example, the blueberry fruit extract can range from about 0.005 wt % to about 90 wt %, the capsicum fruit extract can range from about 0.005 wt % to about 90 wt %, and the turmeric root extract can range from about 0.005 wt % to about 90 wt % of the composition. In yet another example, the blueberry fruit extract, the capsicum fruit extract, and the turmeric root extract can each range from about 0.005 wt % to about 5 wt % of the composition. In a further example, the blueberry fruit extract, the capsicum fruit extract, and the turmeric root extract can each range from about 0.1 wt % to about 2.5 wt % of the composition.

When present, in one example, the apple extract, the grape extract, the green tea extract, the olive extract, the blueberry fruit extract, the capsicum fruit extract, and the turmeric root extract can be present in the composition at a weight ratio of about 1:1:1:1:1:1:1. In another example, at least one of the extracts can be present in a different amount.

In yet a further example, the myeloperoxidase inhibitor can further include turmeric rhizome extract and mangosteen. The mangosteen can include a Garcinia mangostana and can be in the form of a fruit, a fruit extract, a pericarp extract, or a combination thereof. In one example, the mangosteen can include a mangosteen fruit extract, a mangosteen pericarp extract, or a combination thereof. In one example, the turmeric rhizome extract can range from about 0.01 wt % to about 80 wt % and the mangosteen can range from about 0.01 wt % to about 80 wt % of the composition. In another example, the turmeric rhizome extract can range from about 0.005 wt % to about 90 wt % and the mangosteen can range from about 0.005 wt % to about 90 wt % of the composition. In yet another example, the turmeric rhizome extract can range from about 0.0025 wt % to about 95 wt % and the mangosteen can range from about 0.0025 wt % to about 95 wt % of the composition. In yet another example, the turmeric rhizome extract and the mangosteen can each range from about 0.005 wt % to about 5 wt % of the composition. In one example, the apple extract, the grape extract, the green tea extract, the olive extract, the blueberry fruit extract, the capsicum fruit extract, the turmeric root extract, the turmeric rhizome extract, and the mangosteen can be present in the composition at a weight ratio of about 1:1:1:1:1:1:1:1:1. In another example, at least one of the extracts can be present at a different amount than the other extracts.

In one example, the myeloperoxidase inhibitor can further include bergamot fruit extract. In one example, the bergamot fruit extract can be derived from *Citrus bergamia* Risso. In another example, the bergamot fruit extract can range from about 0.01 wt % to about 80 wt % of the composition. In yet another example, the bergamot fruit extract can range from about 0.005 wt % to about 90 wt % of the composition. In a further example, the bergamot fruit extract can range from about 0.0025 wt % to about 90 wt % of the composition. In yet another example, the bergamot fruit extract can comprise from about 0.0025 wt % to about 5 wt % of the composition. In one example, the apple extract, the grape extract, the green tea extract, the olive extract, the blueberry fruit extract, the capsicum fruit extract, the turmeric root extract, the turmeric rhizome extract, the mangosteen, and the bergamot fruit extract can be present in the composition at a weight ratio of about 1:1:1:1:1:1:1:1:1:1.

In yet another example, the myeloperoxidase inhibitor can include sodium copper chlorophyllin, spearmint (*Mentha spicada*) oil, or a combination thereof. In one example, the sodium copper chlorophyllin can be present in the composition from about 10 wt % to about 80 wt %. In another example, the sodium copper chlorophyllin can be present in the formulation from about 5 wt % to about 90 wt %. In one example, the spearmint oil can be present in the composition from about 10 wt % to about 50 wt %. In another example, the spearmint oil can be present in the formulation from about 5 wt % to about 25 wt %.

The ratio of sodium copper chlorophyllin to spearmint oil can also vary in the composition. In one example, the ratio can range from about 1:1 to about 10:1, respectively. In one example, the spearmint oil can be derived from the aerial parts, roots, leaves, flowers, or a combination thereof.

In some examples, the chlorophyllin and spearmint composition can acutely raise NO levels without administering a NOS dependent sources of nitric oxide, such as L-arginine, citrulline and/or without administering a NOS independent source of nitric oxide, such as beet root extract. In some examples, the sodium copper chlorophyllin and the spearmint oil can be administered in a composition alone. In some examples, the composition can include sodium copper chlorophyllin, spearmint oil, proplparben, and methylparaben without a NOS dependent or independent source of nitric oxide. A composition comprising sodium copper chlorophyllin, spearmint (*Mentha spicada*) oil, or a combination thereof, with or without a NOS dependent and independent source of NO, can also be used in any of the methods described herein.

In one specific example of the composition, the NOS dependent source of nitric oxide can include a member selected from the group consisting of L-arginine, L-citrulline, or a combination thereof and the myeloperoxidase inhibitor can include red grape seed extract and pomegranate fruit extract. In yet another example, the NOS dependent source of nitric oxide can include a member selected from the group consisting of L-arginine, L-citrulline, or a combination thereof; the myeloperoxidase inhibitor can include red grape seed extract and pomegranate fruit extract; and the NOS independent source of nitric oxide can include red beet extract and vitamin B1.

In some examples, the composition can further include d-ribose, folic acid, malic acid, vitamin B6, vitamin B12, vitamin D3, magnesium oxide, calcium, inulin, chicory root extract, cherry extract, or a combination thereof. In some examples, the composition can further include a pharmaceutically acceptable carrier. In one example, the composition can further include coatings, isotonic agents, absorption delaying agents, binders, adhesives, lubricants, disintergrants, coloring agents, flavoring agents, sweetening agents, absorbants, detergents, emulsifying agents, antixoidants, vitamins, minerals, proteins, fats, carbohydrates, or a combination thereof. In one example, the composition can further include a sweetener, a preservative, a flavoring, or a combination thereof. In some examples, the formulation can include a polymers for sustained release of a given compound.

In another example, the formulation can include emulsifiers. In one example, the emulsifier can add stability to the final product. Examples of suitable emulsifiers include, but are not limited to, lecithin (e.g., from egg or soy), or mono- and di-glycerides. Other emulsifiers are readily apparent to the skilled artisan and selection of suitable emulsifier(s) will depend, in part, upon the formulation and final product.

In yet another example, the formulation can include a preservative. In one example, the preservatives such as potassium sorbate, sodium sorbate, potassium benzoate, sodium benzoate, or calcium disodium EDTA are used.

In a further example, the nutritional supplement can contain natural or artificial sweeteners, e.g., glucose, sucrose, fructose, saccharides, cyclamates, aspartamine, sucralose, aspartame, acesulfame K, or sorbitol.

In one example, the composition can be in the form of an oral dosage formulation. In another example, the oral dosage formulation can be a capsule, a tablet, a soft gel, a lozenge, a sachet, a powder, a beverage, a syrup, a suspension, or a food. In another example, the compositions can be formulated into a food or drink, and provided, for example, as a snack bar, a cereal, a drink, a gum, or in any other easily ingested form. In one example, the composition can be incorporated into a liquid beverage such as water, milk, juice, or soda. In another example, the composition can be formulated into a nutritional beverage. The nutritional beverage can be in a premixed formulation or can be a powdered mix in that can be added to a beverage. In another example, the powder mix in can be in the form of granules. In one example, the composition can be dried and made readily soluble in water.

In yet another example, the oral dosage form can be in a solution or a suspension in an aqueous liquid or non-aqueous liquid, such as ethanol, glycerol, vegetable oil, salt solutions, or hydroxymethyl cellulose; or in the form of an oil-in-water emulsion or a water-in-oil emulsion, or a combination thereof. In examples where the oral dosage form includes oils, the oils can be edible oils, such as e.g. cottonseed oil, sesame oil, coconut oil, or peanut oil. In some examples, the composition can include suitable dispersing or suspending agents for aqueous suspensions include synthetic or natural gums such as tragacanth, alginate, gum arabic, dextran, sodium carboxymethylcellulose, gelatin, methylcellulose, and polyvinylpyrrolidone.

In another example, the composition can be formulated into a food product. In one example, the food product can be a pudding, confections, (i.e., candy), ice cream, frozen confections and novelties, or non-baked extruded food products such as bars. In one example, the composition can be a powder that is added to non-baked goods. For, example a nutritional bar can be manufactured by adding the powder to the dry ingredients and then incorporating the dry and wet. The wet and dry ingredients can be mixed until the dough phase is reached. The dough can then be put into an extruder and extruded; the extruded dough can be cut into appropriate lengths; and the product can be cooled.

Flavors, coloring agents, spices, nuts, and the like can be incorporated into the product. Flavorings can be in the form of flavored extracts, volatile oils, chocolate flavorings (e.g., non-caffeinated cocoa or chocolate, chocolate substitutes such as carob), peanut butter flavoring, cookie crumbs, crisp rice, vanilla, or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch, or toffee. In one example, the nutritional supplement contains berry or other fruit flavor. The food compositions may further be coated, for example with a yogurt coating if it is as a bar.

In one example, the oral dosage form can include from about 5 mg to about 1,000 mg of the NOS dependent source of nitric oxide, from about 5 mg to about 1,000 mg of the NOS independent source of nitric oxide, and from about 5 mg to about 100 mg of the myeloperoxidase inhibitor. In another example, the oral dosage form can include from about 1 mg to about 100 mg of the NOS dependent source of nitric oxide, from about 1 mg to about 100 mg of the NOS independent source of nitric oxide, and from about 1 mg to about 100 mg of the myeloperoxidase inhibitor. In yet another example, the oral dosage form can include from about 0.5 mg to about 100 mg of the NOS dependent source of nitric oxide, from about 0.5 mg to about 100 mg of the NOS independent source of nitric oxide, and from about 0.5 mg to about 100 mg of the myeloperoxidase inhibitor. In yet another example, the oral dosage form is prepared for administration to the subject according to a predetermined regimen. In a further example, the oral dosage form can be formulated to be administered to the subject once per day.

In one example, the formulation can be in the form of a cream or lotion for topical application. In another example the active ingredient can be in the form of a bolus, electuary, or paste. In yet another example, the composition can be formulated as a depot preparation. In one example, the depot can be for implantation (e.g. subcutaneously, intra-abdominally, or intramuscularly) or intramuscular injection. In one example, the formulation can be formulated as an ion exchange resin.

In one example, the composition can provide an acute increase in biosynthesis of nitric oxide and/or inhibit the activity of myeloperoxidase. In another example, the composition can acutely raise nitric oxide levels in the subject by enhancing biosynthesis production of nitric oxide. In yet another example, the composition can acutely raise nitric oxide levels in the subject by inhibiting myeloperoxidase activity. In a further example, the composition can acutely raise nitric oxide levels in the subject by providing a nitrite/nitrate source for conversion to nitric oxide.

Further presented herein, is a method for acutely raising nitric oxide levels in a subject. In one example, the method can include administering to the subject a therapeutically effective amount of any of the compositions previously presented or within the examples section.

In another example, a method of treating a subject for a condition or disorder that is response to nitric oxide therapy is presented. In one example, the method can include: acutely raising nitric oxide levels in a subject by simultaneously increasing biosynthesis of nitric oxide, increasing nitrate/nitrite levels, and inhibiting myeloperoxidase activity. In one example, the method can include administering a therapeutically effective amount of the composition above, the NOS dependent source of nitric oxide, the NOS independent source of nitric oxide, the myeloperoxidase inhibitor, or a combination thereof.

In one example, the condition or disorder is a nitric oxide related pathology. In another example, the nitric oxide related pathology can include: Alzheimer's disease, angina, asthma, congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia, heart attack, heart failure, hypertension, inflammatory bowel disease, leaky gut, macular degeneration, monocyte-mediated arterial plaque formation, motor dysfunction, multiple sclerosis, obesity, oxidation of LDL, periodontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, and vasculitis.

In a further example, the condition or disorder can be a cardio-metabolic disorder. In one example, the cardio-metabolic disorder can include: Alzheimer's disease, angina, asthma, congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia, heart attack, heart failure, hypertension, inflammatory bowel disease, leaky gut, macular degeneration, monocyte-mediated arterial plaque formation, motor dysfunction, multiple sclerosis, obesity, oxidation of LDL, periodontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, and vasculitis. In yet another example, the cardio-metabolic disorder can include hypertension, cardiovascular dysfunction, neurodegeneration, arthritis, asthma, and septic shock. In a further example, the cardio-metabolic disorder can be preventing the formation of arterial plaque. In one example, the treatment of the cardio-metabolic disorder can be prophylactic.

In one example, the condition or disorder can be a myeloperoxidase related pathology. In another example, the myeloperoxidase-related pathology can be Alzheimer's disease, angina, asthma, general congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia glomerulonephritis, heart attack, heart failure, hypertension, immune deficiency, inflammatory bowel disease, leaky gut, macular degeneration, monocyte-mediated arterial plaque formation, motor dysfunction, multiple sclerosis, obesity, oxidation of LDL, periodontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, vasculitis and diseases associated with skin such as slow wound healing, wrinkles, and premature signs of aging. In a further example, the myeloperoxidase related pathology can be increased oxidized LDL cholesterol. In yet a further example, the myeloperoxidase related pathology can be metabolic syndrome, type 1 diabetes, type 2 diabetes, type 3 diabetes, or a combination thereof. In one example, the myeloperoxidase related pathology can be leaky gut, endotoxemia, inflammatory bowel disease, or a combination thereof. In a further example, the myeloperoxidase related pathology can be a dermatopic pathology including slow wound healing, wrinkles, sun spots, and premature signs of aging.

In some examples, the treatment of the subject can be prophylactic. In one example, the condition or disorder can be penile dysfunction. In some examples, acutely raising of nitric oxide levels in the subject can enhance endothelial functioning, decrease monocyte-mediated arterial plaque formation, decrease the development of peripheral arterial disease, or a combination thereof, wherein an increase or decrease refers to a level in the subject prior to the administering of the therapeutically effective combination.

In one example, the method can be used to treat a mammal. In one example, the mammal can be a human. In another example, the method can be used to treat a domestic animal, such as a dog or cat. In yet another example, the method can be used to treat livestock, such as cows, horses, donkeys, or pigs. The treatment can in some examples be prophylactic. In some examples, acutely raising nitric oxide levels in the subject can raise salivary nitrite levels in the subject beyond a level of the salivary nitrite in the subject as compared to a level prior to administering the therapeutically effective combination.

Further presented herein is a system for acutely raising nitric oxide levels in a subject. In one example, the system can include: an effective amount of a NOS dependent source of nitric oxide, an effective amount of a NOS independent source of nitric oxide, and an effective amount of a myeloperoxidase inhibitor. In one example, the at least one of the NOS dependent source of nitric oxide, the NOS independent source of nitric oxide, and the myeloperoxidase inhibitor can be separate from one another. In another example, the at least one of the NOS dependent source of nitric oxide, the NOS independent source of nitric oxide, and the myeloperoxidase inhibitor can be in separate formulations.

In some examples, the level of nitric oxide in the subject following administration of the composition in the system can be greater than an amount provided by an equivalent amount of any one of the NOS dependent source of nitric oxide, the NOS independent source of nitric oxide, or the myeloperoxidase inhibitor. In another example, the level of nitric oxide can be greater than an additive amount of an equivalent amount of any one of the NOS dependent source of nitric oxide, the NOS independent source of nitric oxide, or the myeloperoxidase inhibitor.

In yet a further example, the system can be formulated as kit. In one example, the kit can include one or more containers filled with one or more of the ingredients of the compositions. Optionally associated with such container(s), can be a notice in the form prescribed by a government agency regulating the manufacture, use or sale of pharmaceutical products, which notice reflects approval by the agency of manufacture, use of sale, and/or approval for human administration. The pack or kit can be labeled with information and instructions regarding mode of administration, sequence of administration (e.g., separately, sequentially, or concurrently), dosing regimen, or the like. The pack or kit may also include means for reminding the patient to take the therapy. The pack or kit can be a single unit dosage of the combination therapy or it can be a plurality of unit dosages. In particular, the agents can be separated, mixed together in any combination, present in a formulation or tablet.

The recommended daily amounts of each ingredient, can serve as a guideline for formulating the compositions and systems of this invention. The actual amount of each ingredient per unit dosage will depend upon the number of units administered daily to the individual in need thereof. This is a matter of product design and is well within the skill of the nutritional supplement formulator.

Figure 8A:
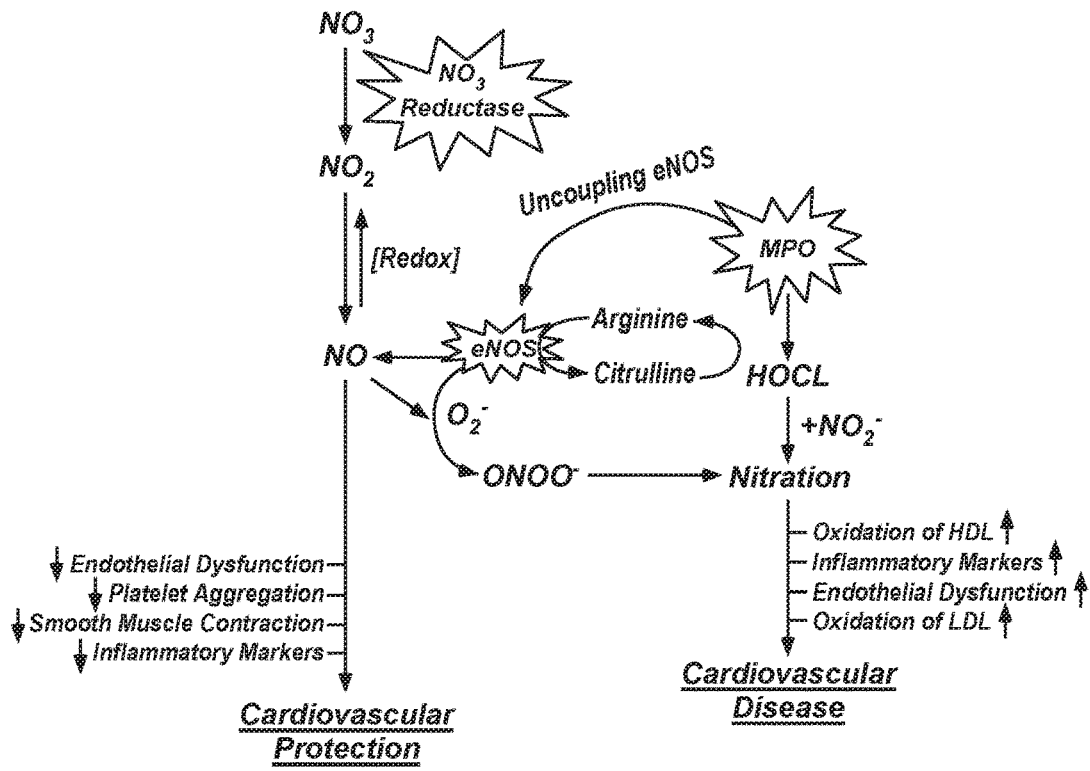
FIG. 8 depicts the multifunctional role of myeloperoxidase in the nitration of key proteins in cardiovascular disease [A] and the three putative sites of action inhibited simultaneously by the novel phytocomplexes described by the instant invention [B]

The phytocomplexes described herein have few obvious physiochemical properties in common. Functionally, however, all have demonstrated a combination of chemical and biological characteristics necessary for attenuating the role of MPO in eNOS biosynthesis of NO. As depicted in FIG. 8A, MPO can functionally uncouple eNOS resulting in the production of singlet state $O_2^-$, as well as, NO by eNOS. The NO and $O_2^-$ can then combine to form peroxynitrite (ONOO.$^-$), which in turn nitrates proteins and disrupts metabolic homeostasis. MPO can also form hypochlorous acid (HOCL) as previously described, which also functions to disrupt metabolic homeostasis through protein nitration.

Figure 8B:
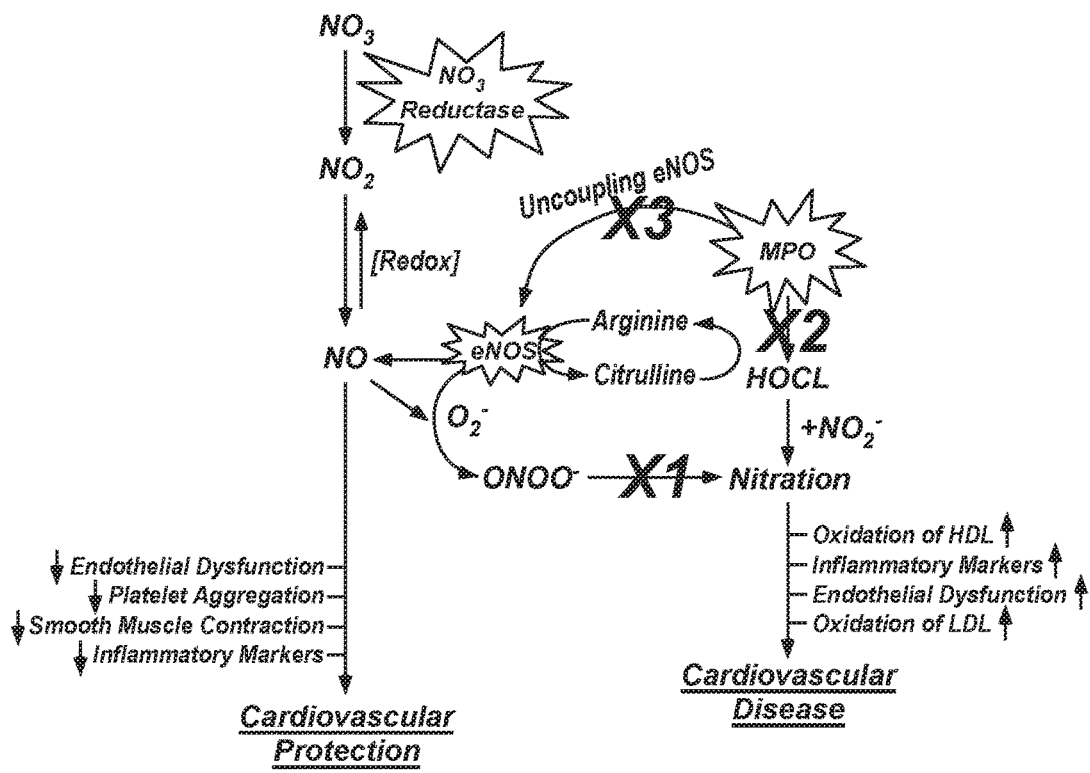

The phytocomplexes of the instant invention all appear to simultaneously function (1) to chemically eliminate ONOO.$^-$ (X1 site in FIG. 8B), (2) to enzymatically inhibit MPO formation of hypochlorite (X2 site in FIG. 8B), and (3) to enzymatically inhibit MPO uncoupling of eNOS (X3 site in FIG. 8B). This novel, muti-targeted effect of the phytocomplexes described herein offers a cogent explanation for the ability of formulations that do not contain dietary $NO_3$ or the amino acids arginine and citrulline to rapidly increase NO. Inhibiting the uncoupling of eNOS by MPO would prevent the loss of NO through the $O_2^-$ and ONOO.$^-$ pathway. Similarly, the phytocomplexes would be expected to enhance the effects of either dietary $NO_3$ or arginine and citrulline, as was demonstrated herein in clinical studies. Thus, a unique multi-targeted property of specific phytocomplexes has been discovered with uses in the rapid enhancement of NO biosynthesis or bioavailability.

EMBODIMENTS

In one embodiment presented herein, is a composition for acutely raising nitric oxide levels in a subject, comprising: an effective amount of a NOS dependent source of nitric oxide; an effective amount of a NOS independent source of nitric oxide; and an effective amount of a myeloperoxidase inhibitor; wherein the composition acutely raises nitric oxide levels in a subject above a level provided by the available sources of nitric oxide in the subject prior to administration of the composition.

In one embodiment of the composition, the level of nitric oxide in the subject following administration of the composition is greater than an amount provided by an equivalent amount of any one of the NOS dependent source of nitric oxide, the NOS independent source of nitric oxide, or the myeloperoxidase inhibitor.

In one embodiment of the composition, the NOS dependent source of nitric oxide comprises from about 1 wt % to about 80 wt % of the composition.

In one embodiment of the composition, the NOS dependent source of nitric oxide comprises a member selected from the group consisting of L-arginine, L-citrulline, ornithine, or a combination thereof.

In one embodiment of the composition, the NOS dependent source of nitric oxide comprises L-arginine.

In one embodiment of the composition, the L-arginine in the composition ranges from about 1 wt % to about 80 wt %.

In one embodiment of the composition, the NOS dependent source of nitric oxide comprises L-citrulline.

In one embodiment of the composition, the L-citrulline in the composition ranges from about 1 wt % to about 80 wt %.

In one embodiment of the composition, a source of the L-citrulline comprises watermelon extract.

In one embodiment of the composition, the NOS dependent source of nitric oxide comprises L-arginine and L-citrulline.

In one embodiment of the composition, the L-arginine and the L-citrulline each comprise from 1 wt % to about 80 wt %.

In one embodiment of the composition, the L-arginine and L-citrulline are present in the composition at a weight percent concentration range from about 1:5 to about 5:1, respectively.

In one embodiment of the composition, the L-arginine and L-citrulline are present in the composition at a weight percent concentration ratio of about 2:1, respectively.

In one embodiment of the composition, the NOS independent source of nitric oxide comprises a member selected from the group consisting of beet root extract, vitamin B1, collard green extract, nut powders, spinach extract, broccoli extract, lettuce extract, celery, kale, watercress, carrot, arugula, mustard greens, or a combination thereof.

In one embodiment of the composition, the NOS independent source of nitric oxide comprises beet root extract, vitamin B1, or a combination thereof.

In one embodiment of the composition, the NOS independent source of nitric oxide comprises the beet root extract and the vitamin B1.

In one embodiment of the composition, the beet root extract comprises from about 5 wt % to about 90 wt % and wherein the vitamin B1 comprises from about 0.01 wt % to about 80 wt % of the composition.

In one embodiment of the composition, the beet root extract and vitamin B1 are present in the composition at a weight percent concentration ratio ranging from about 50:1 to about 10:1, respectively.

In one embodiment of the composition, the myeloperoxidase inhibitor comprises from about 1 wt % to about 90 wt %.

In one embodiment of the composition, the myeloperoxidase inhibitor comprises a member selected from the group consisting of pomegranate fruit extract, red grape polyphenols, apple extract, blueberry extract, capsicum extract, grape extract, green tea extract, olive extract, bergamot extract, mangosteen, or a combination thereof.

In one embodiment of the composition, the mangosteen can comprise a member selected from the group consisting of mangosteen fruit, mangosteen extract, or a combination thereof.

In one embodiment of the composition, the myeloperoxidase inhibitor comprises a member selected from the group consisting of pomegranate fruit extract, red grape polyphenols, or a combination thereof.

In one embodiment of the composition, the myeloperoxidase inhibitor comprises pomegranate fruit extract, and red grape polyphenols.

In one embodiment of the composition, the pomegranate fruit extract comprises from about 1 wt % to about 80 wt % and wherein the red grape polyphenols comprises from about 1 wt % to about 80 wt % of the composition.

In one embodiment of the composition, the myeloperoxidase inhibitor comprises apple extract, grape extract, green tea extract, and olive extract.

In one embodiment of the composition, the apple extract, grape extract, green tea extract, and olive extract collectively comprise from about 1 wt % to about 80 wt % of the composition.

In one embodiment of the composition, the apple extract comprises from about 0.01 wt % to about 80 wt %, the grape extract comprises from about 0.01 wt % to about 80 wt %, the green tea extract comprises from about 0.01 wt % to about 80 wt % and the olive extract comprises from about 0.01 wt % to about 80 wt % of the claimed composition.

In one embodiment of the composition, the apple extract, grape extract, green tea extract, and olive extract are present in the composition at a weight ratio of about 1:1:1:1.

In one embodiment of the composition, the apple extract, grape extract, green tea extract, and olive extract are present in the composition at a weight ratio of about 6:1:3:1.

In one embodiment of the composition, at least one of the apple extract, the grape extract, the green tea extract, and the olive extract are present in the composition in a different amount.

In one embodiment of the composition, the grape extract comprises grape seed extract and grape skin extract.

In one embodiment of the composition, the myeloperoxidase inhibitor further comprises pomegranate fruit extract.

In one embodiment of the composition, the myeloperoxidase inhibitor further comprises blueberry fruit extract, capsicum fruit extract, and turmeric root extract.

In one embodiment of the composition, the blueberry fruit extract comprises from about 0.01 wt % to about 80 wt %, the capsicum fruit extract comprises from about 0.01 wt % to about 80 wt %, and the turmeric root extract comprises from about 0.01 wt % to about 80 wt % of the composition.

In one embodiment of the composition, the apple extract, the grape extract, the green tea extract, the olive extract, the blueberry fruit extract, the capsicum fruit extract, and the turmeric root extract are present in the composition at a weight ratio of about 1:1:1:1:1:1:1.

In one embodiment of the composition, the composition can further comprises turmeric rhizome extract, and mangosteen extract.

In one embodiment of the composition, the turmeric rhizome extract comprises from about 0.1 wt % to about 80 wt % and the mangosteen extract comprises from about 0.1 wt % to about 80 wt % of the composition.

In one embodiment of the composition, the apple extract, the grape extract, the green tea extract, the olive extract, the blueberry fruit extract, the capsicum fruit extract, the turmeric root extract, the turmeric rhizome extract, and the mangosteen are present in the composition at a weight ratio of about 1:1:1:1:1:1:1:1:1.

In one embodiment of the composition, the mangosteen comprises a mangosteen fruit, a mangosteen pericarp, a manogsteen extract, or a combination thereof.

In one embodiment of the composition, the formulation further comprises bergamot fruit extract.

In one embodiment of the composition, the bergamot fruit extract comprises from about 0.01 wt % to about 80 wt % of the composition.

In one embodiment of the composition, the myeloperoxidase inhibitor can comprise sodium copper chlorophyllin, spearmint oil, or a combination thereof.

In one embodiment of the composition, the NOS dependent source of nitric oxide comprises a member selected from the group consisting of L-arginine, L-citrulline, or a combination thereof and wherein the myeloperoxidase inhibitor comprises red grape seed extract and pomegranate fruit extract.

In one embodiment of the composition, the composition further comprises a member selected from the group consisting of d-ribose, folic acid, malic acid, vitamin B6, vitamin B12, vitamin D3, magnesium oxide, calcium, inulin, chicory root extract, cherry extract, or a combination thereof.

In one embodiment of the composition, the composition further comprises a pharmaceutically acceptable carrier.

In one embodiment of the composition, the composition further comprises a member selected from the group consisting of a sweetener, a preservative, a flavoring, or a combination thereof.

In one embodiment of the composition, the composition is an oral dosage formulation In one embodiment of the composition, the oral dosage form comprises a capsule, a tablet, a powder, a beverage, a syrup, a suspension, or a food.

In one embodiment of the composition, the oral dosage form comprises from about 5 mg to about 1,000 mg of the NOS dependent source of nitric oxide, from about 5 mg to about 1,000 mg of the NOS independent source of nitric oxide, and from about 5 mg to about 1,000 mg of the myeloperoxidase inhibitor.

In one embodiment of the composition, the oral dosage form is prepared for administration to the subject according to a predetermined regimen.

In one embodiment of the composition, the oral dosage form is administered to the subject once per day.

In one embodiment of the composition, the composition acutely raises nitric oxide levels in the subject by enhancing biosynthesis production of nitric oxide.

In one embodiment of the composition, composition acutely raises nitric oxide levels in the subject by inhibiting myeloperoxidase activity.

In one embodiment of the composition, the composition acutely raises nitric oxide levels in the subject by providing a nitrite/nitrate source for conversion to nitric oxide.

In another embodiment presented herein is a method for acutely raising nitric oxide levels in a subject, comprising: administering to the subject a therapeutically effective amount of any one of the compositions recited above.

In yet another embodiment presented herein, is a method of treating a subject for a condition or disorder that is response to nitric oxide therapy, comprising: acutely raising nitric oxide levels in a subject by simultaneously increasing biosynthesis of nitric oxide, increasing nitrate/nitrite levels, and inhibiting myeloperoxidase activity.

In one embodiment of the method, the condition or disorder is a nitric oxide related pathology.

In one embodiment of the method, the nitric oxide related pathology comprises a member selected from the group consisting of Alzheimer's disease, angina, asthma, congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia, heart attack, heart failure, hypertension, inflammatory bowel disease, leaky gut, macular degeneration, monocyte-mediated arterial plaque formation, motor dysfunction, multiple sclerosis, obesity, oxidation of LDL, peridontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, and vasculitis.

In one embodiment of the method, the condition or disorder is a cardio-metabolic disorder.

In one embodiment of the method, the cardio-metabolic disorder comprises a member selected from the group consisting of: Alzheimer's disease, angina, asthma, congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia, heart attack, heart failure, hypertension, inflammatory bowel disease, leaky gut, macular degeneration, monocyte-mediated arterial plaque formation, motor dysfunction, multiple sclerosis, obesity, oxidation of LDL, peridontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, and vasculitis.

In one embodiment of the method, the cardio-metabolic disorder comprises a member selected from the group consisting of hypertension, cardiovascular dysfunction, neurodegeneration, arthritis, asthma, and septic shock.

In one embodiment of the method, the cardio-metabolic disorder comprises preventing the formation of arterial plaque.

In one embodiment of the method, the treating of the subject is prophylactic.

In one embodiment of the method, the condition or disorder is a myeloperoxidase related pathology.

In one embodiment of the method, the myeloperoxidase-related pathology is Alzheimer's disease, angina, asthma, general congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia glomerulonephritis, heart attack, heart failure, hypertension, immune deficiency, inflammatory bowel disease, leaky gut, macular degeneration, monocyte-mediated arterial plaque formation, motor dysfunction, multiple sclerosis, obesity, oxidation of LDL, peridontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, vasculitis and diseases associated with skin such as slow wound healing, wrinkles, and premature signs of aging.

In one embodiment of the method, the myeloperoxidase related pathology comprises increased oxidized LDL cholesterol.

In one embodiment of the method, the myeloperoxidase related pathology comprises metabolic syndrome, type 1 diabetes, type 2 diabetes, type 3 diabetes, or a combination thereof.

In one embodiment of the method, the myeloperoxidase related pathology comprises leaky gut, endotoxemia, inflammatory bowel disease or a combination thereof.

In one embodiment of the method, the myeloperoxidase related pathology comprises a dermatopic pathology including slow wound healing, wrinkles, sun spots, and premature signs of aging.

In one embodiment of the method, the treating of the subject is prophylactic.

In one embodiment of the method, the condition or disorder is penile dysfunction.

In one embodiment of the method, acutely raising of nitric oxide levels in the subject enhances endothelial functioning, decreases monocyte-mediated arterial plaque formation, decreases the development of peripheral arterial disease, or a combination thereof, wherein an increase or decreases refers to a level in the subject prior to the administering of the therapeutically effective combination.

In one embodiment of the method, the subject is a human.

In one embodiment of the method, the treating of the subject is prophylactic.

In one embodiment of the method, acutely raising nitric oxide levels in the subject comprises raising salivary nitrite levels in the subject beyond a level of the salivary nitrite in the subject as compared to a level prior to administering the therapeutically effective combination.

In another embodiment presented herein is a system for acutely raising nitric oxide levels in a subject, comprising: an effective amount of a NOS dependent source of nitric oxide; an effective amount of a NOS independent source of nitric oxide; and an effective amount of a myeloperoxidase inhibitor.

In one embodiment of the system, at least one of the NOS dependent source of nitric oxide, the NOS independent source of nitric oxide, and the myeloperoxidase inhibitor are separate from one another.

In one embodiment of the system, at least one of the NOS dependent source of nitric oxide, the NOS independent source of nitric oxide, and the myeloperoxidase inhibitor are in separate formulations.

In one embodiment of the system, a level of nitric oxide in the subject following administration of the composition is greater than an amount provided by an equivalent amount of any one of the NOS dependent source of nitric oxide, the NOS independent source of nitric oxide, or the myeloperoxidase inhibitor.

In one embodiment of the system, the level of nitric oxide is greater than an additive amount of an equivalent amount of any one of the NOS dependent source of nitric oxide, the NOS independent source of nitric oxide, or the myeloperoxidase inhibitor.

In one embodiment of the system, the system is formulated as a kit.

In one embodiment presented herein is, a composition for acutely raising nitric oxide levels in a subject, comprising an effective amount of sodium copper chlorophyllin, spearmint oil, or a combination thereof.

In one embodiment, the composition comprises sodium copper chlorophyllin and spearmint oil.

In one embodiment, the composition comprises a weight ratio of sodium copper chlorophyllin to spearmint oil ranges from about 1:1 to about 10:1.

In one embodiment, the composition comprises spearmint oil and the spearmint oil is derived from the aerial parts, roots, leaves, flowers, or a combination thereof.

In one embodiment, a method of treating a subject for a condition or disorder that is response to nitric oxide therapy, comprising inhibiting myeloperoxidase activity is provided.

In one embodiment, the method can comprise administering a therapeutically effective amount of sodium copper chlorophyllin, spearmint oil, or a combination thereof to the subject.

EXAMPLES

Example 1

Acute Nitric Oxide Production by an Arginine/Citrulline/Phytochemical Formulation Two NO-generating formulations, shown below, were tested to assess their acute, enhanced biosynthesis of the NO biomarker, $NO_2$ in saliva in subjects with normal plasma concentrations of ADMA.

TABLE 2

Active Ingredients in Test Formulations

| | Formula 1 | | Formula 2 | |
|---|---|---|---|---|
| Active Ingredient | [mg] | [Active Fraction] | [mg] | [Active Fraction] |
| L-Arginine | 5,300 | 0.92 | 5,008 | 0.87 |
| L-Citrulline | 250 | 0.043 | 209 | 0.036 |
| Pomegranate Juice Concentrate | 50 | 0.0087 | 491 | 0.085 |
| Grape Skin Extract | 185 | 0.0321 | 73.6 | 0.0126 |
| Red Grape Polyphenol | 0.00 | 0.00 | 49.1 | 0.87 |

Methods—

The Nitrate/Nitrite Fluorometric Assay Kit (Cayman Chemicals Item No: 780051, Ann Arbor, Mich.) was used to measure the $NO_3/NO_2$ content of the formulations. Fluorescence was analyzed with an excitation wavelength of 375 nm and an emission wavelength of 417 nm using a Cytation5 microplate fluorometer (Bio Tek Instruments, Winooski, Vt.). The assay has a reported limit of detection for $NO_3$ of approximately 0.2 μM in the final solution.

Over three days, subjects, with normal plasma concentrations of ADMA, were instructed to consume the 10 g of either F1 or F2 with 500 mL of water subsequent to developing the first, pre-dose NO strip. At post-dosing times 30, 60 and 90 minutes, NO strips were again developed for all subjects. One subject was given a 2× dose (20 g) of both formulations over the experimental period. The salivary NO strips, which detect salivary $NO_2$, were nitric Oxide Test Strips (Berkeley Test, Berkeley, Calif.). Color development of NO strips was quantitated using densitometry. Means and 95% confidence intervals were computed using Excel [Microsoft, Redman, Wash.].

Results—

Figure 9A:
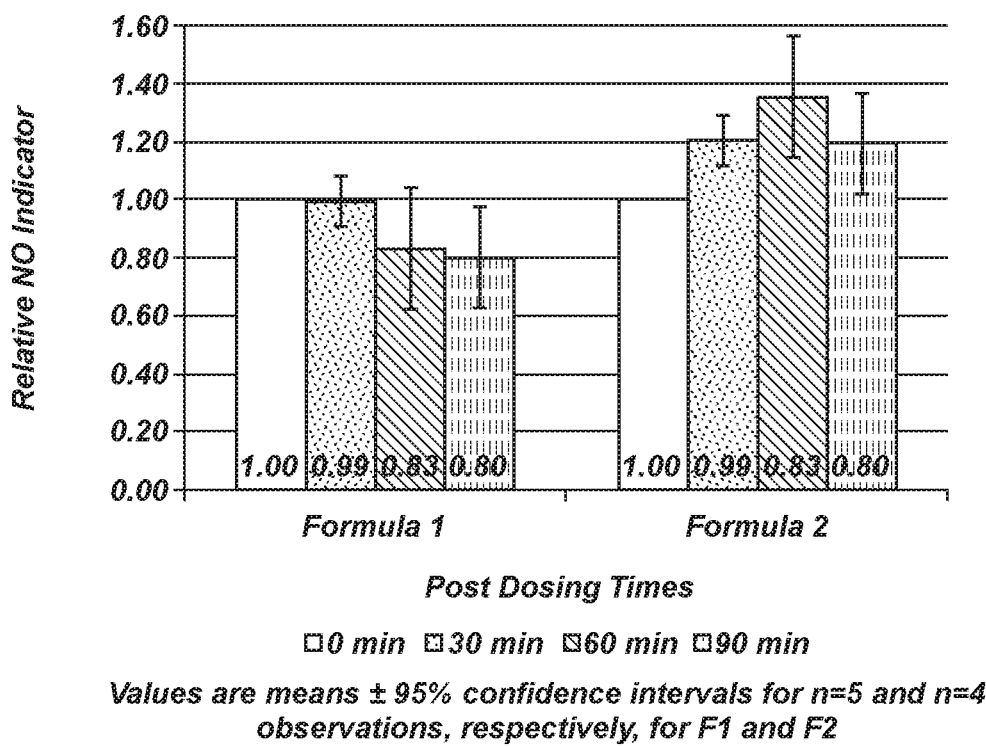
FIG. 9 graphically presents the relative salivary NO biomarker concentrations at 0, 30, 60, and 90 minutes post-dosing for [A] n=5 and n=4 subjects, respectively, for F1 and F2 and [B] a single individual consuming a double-dose of F1 and F2 on two different occasions, in accordance with Examples 1 & 2.

As seen in FIG. 9A, F2 unexpectedly produced an average increase of 21% relative to F1 at 30 min (p<0.5). The acute increase in NO biomarker with F2 continued with a 35% increase relative to zero time F2 and 66% relative to F1 at 60 min (p<0.05). While F2 NO biomarker levels remained 19% above F2 zero time at 90 min, NO2 levels were 49% above F1 concentrations (p<0.05) at this final time point.

Figure 9B:
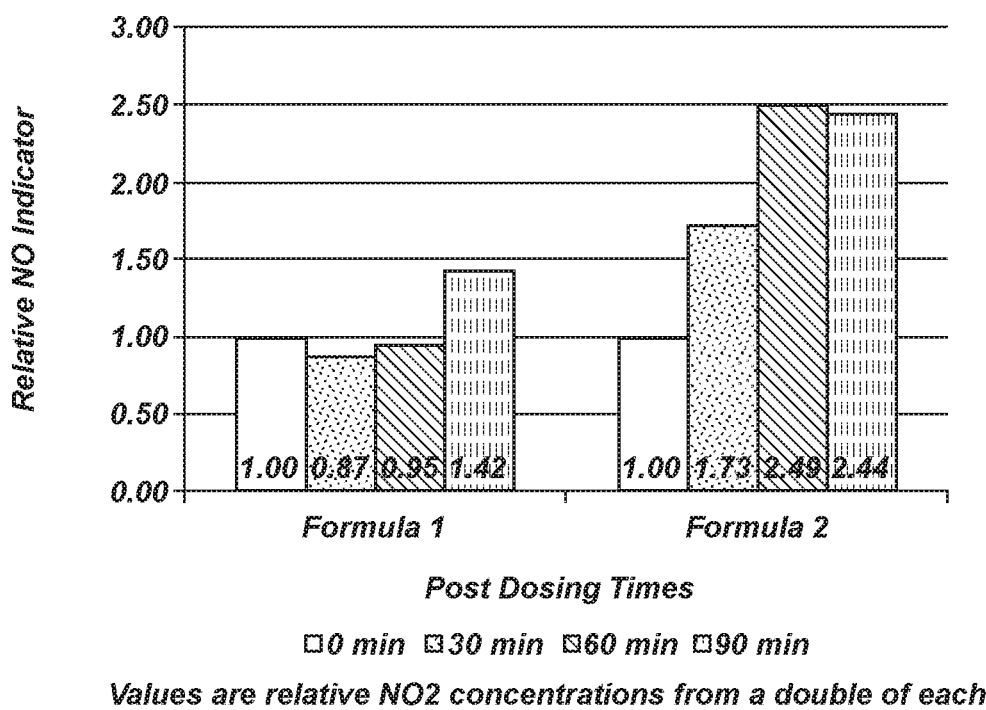

NO biomarker results for the subject consuming the double-dose of both F1 and F2 are presented in FIG. 9B. As seen with single-doses, F2 produced an acute NO strip response of 73% within 30 min that continued increasing through 60 min to 2.5-times the pre-dose value. Unlike the single-dose, however, the NO biomarker concentration did not fall at 90 min, but remained at the 60-min level. Interestingly, the double dose of F1 resulted in a 42% increase in NO biomarker at 90 min post-dosing, but remained at pre-dose levels at 30 and 60 min post-dosing.

Nitrate levels for F1 and F1 were below the limit of detection of the assay. Samples of pomegranate juice concentration and red grape polyphenol contained, respectively, 24 and 70 μg $NO_3$/g. The addition of pomegranate juice concentration and red grape polyphenol to F2 only increased the NO3 concentration to approximately 1 mg/10 g dosing. Based upon current pharmacodynamic studies in this laboratory, sample $NO_3$ content below 12.5 mg $NO_3$/dose do not produce a detectable increase in NO strip color development. Therefore, it is unlikely that the level of $NO_3$ in F2 could be responsible for the acute increase in NO biomarker observed for F2.

A unique blend of arginine, citrulline and antioxidants produced an acute increase in the salivary NO biomarker $NO_2$, indicative of a rapid biosynthesis of NO.

Example 2

Synergistic Inhibition of Myeloperoxidase Activity by an Arginine/Citrulline Formulation Formulations 1 and 2, as described in Table 2 above, were tested for their synergistic activity. Additional samples of F1 and F2 were prepared at an initial concentration of 100 mg/mL in an acetone:water (1:1) solution, sonicated in an ice bath for 60 min with vortexing every 10 min, and centrifuged at 3000 rpm at ambient temperature for 5 min. The supernatant liquid was transferred to fresh tubes and centrifuged again at 13,300 rpm at ambient temperature for 10 min. This final supernatant fraction was transferred to fresh tubes and stored at −80° C. until assayed.

The acetone used in this example was obtained through Fisher Chemical Co (Pittsburgh, Pa.) and was the highest purity available. All other chemicals and reagents were supplied with the Myeloperoxidase Inhibitor Screening Assay Kit. The Myeloperoxidase Control was stored at −20° C., while the remainder of the kit was stored at −4° C. The positive control 4-aminobenzyhdrazide, supplied with the kit, was run with each assay.

Methodology—

The Myeloperoxidase Inhibitor Screening Assay Kit Item No. 700170 from Cayman Chemical (Ann Arbor, Mich.) was used to assess the ability of the two arginine/citrulline formulations and their components individually to inhibit the production of hypochlorous acid by MPO, as can be seen in FIGS. 9 (A&B).

The chlorination assay utilizes the non-fluorescent 2-[6-(4-aminophenoxy)-3-oxo-3H-xanthen-9-yl]-benzoic acid (APF), which is selectively cleaved by hypochlorite to yield the highly fluorescent compound fluorescein. Fluorescein fluorescence was analyzed with an excitation wavelength of 480-495 nm and an emission wavelength of 515-525 nm using a Cytation5 microplate fluorescence reader (Bio Tek Instruments, Winooski, Vt.).

Calculations—

The median inhibitory concentration (IC50) for the inhibition of MPO activity was calculated using CalcuSyn (BIOSOFT, Ferguson, Mo.). This statistical package performs multiple drug dose-effect calculations using the median effect methods described by T-C Chou and P. Talaly [Chou, T-C, Talaly, P. (1984) *Quantitative analysis of dose-effect relationships: the combined effects of multiple drugs or enzyme inhibitors. Adv Enzyme Regul* 22, 27-55].

Briefly, the analysis correlates the "Dose" and the "Effect" in the simplest possible form: fa/fu=(C/Cm)m, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve; it is estimated by the slope of the median-effect plot.

The median-effect plot is a graph of x=log(C) vs y=log (fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems r>0.85.

Synergy of test components was then quantified using the combination index (CI) parameter. This parameter defines only the additive effect rather than synergism or antagonism. Synergy, however, was defined as a more than expected additive effect (CI>1), and antagonism as a less than expected additive effect (CI<1) as described below.

Expected median inhibitory concentrations of any multi-component combination were estimated using the relationship:

[1/Expected IC50]=[$Fa$/IC50$A$]+ [$Fb$/IC50$B$]+ . . . +[$Fn$/IC50$N$]

Fa=mole fraction of component A in the combination and Fn=the mole fraction of the $n^{th}$ component combination where Fa+Fb+ . . . +Fn=1 and where IC50A=the observed IC50 of the component A, etc.

The CI was then calculated thusly, CI=Expected [IC50]/Observed [IC50]. Using the designation of CI=1 as the additive effect, we obtain for mutually exclusive compounds that have the same mode of action or for mutually non-exclusive drugs that have totally independent modes of action the following relationships: CI<1, =1, and >1 indicating antagonism, additivity and synergy, respectively.

Results—

The observed median inhibitory concentration ($IC_{50}$) of F1 was 9.31 μg/mL, while the calculated, expected $IC_{50}$ was 8.57 μg/mL resulting in a CI=0.92. Thus, the Formulation F1 was no better inhibiting MPO than the sum of its active components (Table 3). On the other hand, Formula 2 inhibited MPO more effectively than the sum of its components with an observed IC50 of 3.57 μg/mL versus an expected IC50 of 8.92 and a CI=2.50 (Table 4).

TABLE 3

Combination Index of Formulation 1 for Myeloperoxidase Inhibition

| Test Material | Observed $IC_{50}$† [μg/mL] | Fraction of Formulation 1 |
|---|---|---|
| L-Arginine | 8.09 (6.20-10.6) | 0.909 |
| L-Citrulline | 18.0 (13.7-23.6) | 0.043 |
| Pomegranate Juice Concentrate | 135 (92.3-197) | 0.0086 |
| Grape Skin Extract | 34.5 (1.17-1.54) | 0.0317 |
| Red Grape Polyphenol | 1.35 (1.18-1.55) | 0.00 |

| | Expected $IC_{50}$ [μg/mL] | Combination Index [Expected $IC_{50}$/ Observed $IC_{50}$] |
|---|---|---|
| Formula F1 | 9.31* (8.05-10.8) | 8.57 | 0.921 |

†Parenthetic values are 95% confidence interval.
*Observed IC50 of the Formulation1 is not different from the Expected IC50 with a CI = 0.921 indicating a lack of synergy.

TABLE 4

Combination Index of Formulation 2 for Myeloperoxidase Inhibition

| Test Material | Observed $IC_{50}$† [μg/mL] | Fraction of Formulation 2 |
|---|---|---|
| L-Arginine | 8.09 (6.20-10.6) | 0.859 |
| L-Citrulline | 18.0 (13.7-23.6) | 0.036 |
| Pomegranate Juice Concentrate | 135 (92.3-197) | 0.084 |
| Grape Skin Extract | 34.5 (1.17-1.54) | 0.0126 |
| Red Grape Polyphenol | 1.35 (1.18-1.55) | 0.0087 |

| | Expected $IC_{50}$ [μg/mL] | Combination Index [Expected $IC_{50}$/ Observed $IC_{50}$] |
|---|---|---|
| Formula F2 | 3.57* (2.63-4.84) | 8.92 | 2.50 |

†Parenthetic values are 95% confidence interval.
*Observed $IC_{50}$ significantly lower (p < 0.05) than the expected IC50 and CI = 2.50 indicating synergy of the five-component formulation.

Conclusion—

With a CI=2.50, F2 unexpectedly inhibited MPO 2.5-times more effectively than the sum of its components indicating synergy of the combination. F1 did not inhibit MPO more or less effectively than the sum of its components representative of an additive response.

Example 3

Acute Nitric Oxide Production by a Copper Chlorophyllin/Spearmint Oil Formulation A liquid chlorophyllin/spearmint oil, shown below, was tested to assess the acute, biosynthesis of the NO biomarker $NO_2$ in saliva in subjects with normal plasma concentrations of ADMA.

TABLE 5

Ingredients in Test Formulation 3

| Ingredient | Formula 3 [mg] | [Active Fraction] |
|---|---|---|
| Propylparaben [NF] | 189 | — |
| Methylparaben | 476 | — |
| Spearmint Aerial Parts Oil (active) | 414 | 0.226 |
| Sodium Copper Chlorophyllin (active) | 1,419 | 0.774 |

Ingredients listed were dissolved in 473.1 mL of purified water.

Methods—

The assay of nitrite in saliva and nitrate in Test Formulation 3 (F3) was conducted as described in Example 1. Color development of NO strips was quantitated as described in Example 1. Means and 95% confidence intervals were computed as described in Example 1.

During the morning period, subjects (n=5), with normal plasma concentrations of ADMA, were instructed to consume 5 mL of the F3 with 500 mL of water subsequent to developing the first, pre-dose NO strip. At post-dosing times 30, 60 and 90 minutes, NO strips were again developed for all subjects.

Results—

Figure 10:
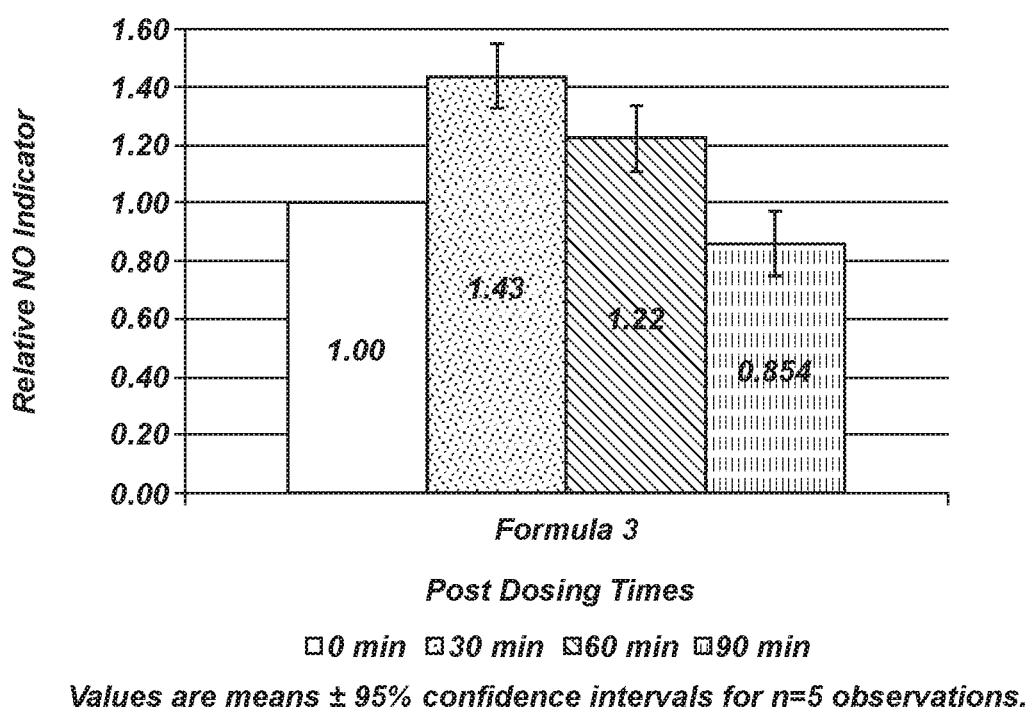
FIG. 10 graphically presents the relative salivary NO biomarker concentrations at 0, 30, 60, and 90 minutes following post-dosing of F3 for n=5 subjects in accordance with Example 3.

As seen in FIG. 10, F3 unexpectedly produced an average, acute increase of 42% relative to zero time at 30 min ($p<0.05$). The acute increase in NO biomarker with F3 continued with a 22% increase relative to zero time at 60 min ($p<0.05$) and returned to approximately 15% below pre-test concentrations at 90 min. The blend of sodium copper chlorophyllin and spearmint oil (aerial parts) produced an acute increase in the salivary NO biomarker $NO_2$, indicative of a rapid biosynthesis of NO.

Example 4

Synergistic Inhibition of Myeloperoxidase Activity by a Ten-Component Phytocomplex A 10-component phytocomplex was tested for synergy in in vitro inhibition of MPO. All chemicals, methods, samples, assay, and calculations were performed as described in Example 2.

The PC10 test material was formulated by combining apple fruit extract, bergamot fruit extract, blueberry fruit concentrate, capsicum fruit, grape seed extract, grape skin extract, green tea leaf extract, mangosteen pericarp extract, olive leaf extract, and turmeric root & rhizome extract in a number of the ratios beginning with 1:1:1:1:1:1:1:1:1:1 and increasing or decreasing the relative amount of a component originally based upon antioxidant activity and cost of ingredient to arrive at the 6:50:1:1:1:1:3:1:1:6 ratio exhibiting the best overall synergy. This formulation served as the basis for testing MPO inhibition and is listed in Table 6.

TABLE 6

Ten-component Phytocomplex (PC10)

| Test Material | Observed $IC_{50}$ [μg/mL] | Relative Amount [F] |
|---|---|---|
| Apple fruit† | 3.86 (3.19-4.66) | 0.085 |
| Bergamot fruit† | 42.0 (28.5-61.7) | 0.704 |
| Blueberry fruit* | 140 (92.4-212) | 0.014 |
| Capsicum fruit† | 34.5 (31.5-42.3) | 0.014 |
| Grape seed† | 2.40 (1.81-3.18) | 0.014 |
| Grape skin† | 34.5 (28.9-41.1) | 0.014 |
| Green tea leaf† | 0.883 (0.557-1.40) | 0.042 |
| Mangosteen pericarp† | 3.35 (2.46-4.56) | 0.014 |
| Olive leaf† | 8.82 (6.27-12.4) | 0.014 |
| Turmeric root & rhizome† | 95.5 (75.0-122) | 0.085 |

| | Expected $IC_{50}$ [μg/mL] | Combination Index [Expected $IC_{50}$/ Observed $IC_{50}$] |
|---|---|---|
| Phytocomplex (PC10) | 2.95* (2.17-4.03) | 10.00 | 3.39 |

†extract/
*concentrate/
** Phytocomplex PC10 contains relative amounts

Results—

As seen in Table 6 above, the observed IC50 of the ten-component phytocomplex was 2.95 μg/mL, while the calculated, expected IC50 value was 10.0 μg/mL resulting in a combination index (CI) of 3.39.

Conclusion—

The ten-component phytocomplex (PC10) in the ratios of about 6:50:1:1:1:1:3:1:1:6 exhibited a dramatic, unexpected increase 3.4-times the MPO-inhibitory activity of its individual components thus exhibiting synergy of the formulation.

Example 5

Clinical Assessment of PC10 in Normal and Pre-Diabetic Subjects

The clinical safety and efficacy of the PC10 formula was determined in an open-label, observational clinical trial. The study population included males and females between the ages of 18 to 72 inclusive exhibiting the following lipid variables: serum triglycerides ≥150 mg/dl and/or serum low density lipoprotein cholesterol (calculated) ≥150 mg/dl. During the 12-week study, subjects were assigned to one of three groups to receive, respectively, 500, 750, or 1000 mg of PC10 to be taken as 2, 3, or 4 capsules taken once daily with the evening meal.

Subjects were instructed to maintain their current lifestyles including diet, exercise, and mind body spirit practices without change during trial participation. Subjects were also instructed not to make changes to their current prescription, non-prescription medications, medical foods or nutritional supplements while on the study.

At one, two and three months, blood was drawn for analysis including complete blood count (CBC), complete metabolic panel (CMP), fasting lipid panel including total cholesterol, triglycerides, HDLc, LDLc, oxLDL, MPO, PAI-1 and HbA1c.

During this 12-week trial, there were no reported adverse events related to the PC10 in the 500, 750, or 1000 mg/day groups (N=35). Efficacy was assessed only for the potential commercial formulation of 500 mg PC10 (n-11).

Table 7 summarizes the changes (Initial—3 Months) in median lipid variables in subjects consuming 500 mg daily of the PC10 formulation over three months. Statistically significant changes were noted in Total Cholesterol, Total Cholesterol/HDL ration, LDL-c (calculated), Apo B and non-HDL for the group of eleven. The change in Total Cholesterol of 7% and LDL-c (calculated) of 10% are considered clinically meaningful.

Additionally, a subgroup analysis was conducted for subjects with a HbA1C≥5.5% (all of whom were insulin resistant with HOMA scores greater than 2). Statistically significant changes were noted in Total Cholesterol, Total Cholesterol/HDL ration, LDL-c (calculated), Apo B, LDL-c (calculated)/HDL ratio, oxLDL, oxLDL/HDL ratio, non-HDL, Triglycerides, TG/HDL ratio and plasminogen activator inhibitor-1 (PAI-1) in this group of eight subjects. The change in Total Cholesterol of 10%, LDL-c (calculated) of 10%, oxLDL of 19%, TG of 27% and PAI-1 of 37% are clinically meaningful and demonstrate the broad spectrum of action of the PC10 formulation.

TABLE 7

Median Changes in Lipid Biomarkers in all Subjects and Subset of Subjects with Elevated HbA1c Consuming 500 mg Daily of The PC10 Formulation over Three Months

| | Total (n = 11) | | HbA1c >5.4 (n = 8)† | |
|---|---|---|---|---|
| Variable | Median Change (% Change) | P* | Median Change (% Change) | P* |
| Weight | 0.0 (0.0) | NS | 1.0 (0.0) | NS |
| Total Cholesterol | −20 (−7.0) | 0.003 | −23 (−10) | 0.008 |
| HDL | −10 (−3.0) | NS | 4.0 (8.0) | NS |
| Cholesterol/HDL | −2.0 (−26) | 0.024 | −2.5 (−45) | 0.016 |
| LDL | −19 (−10) | 0.012 | −21 (−10) | 0.031 |
| oxLDL | −6.0 (−10) | NS | −14 (−19) | 0.047 |
| APOB | −4.0 (−3.0) | 0.037 | −7.0 (−4.0) | 0.016 |
| oxLDL/HDL | −0.2 (−17) | NS | −0.3 (−25) | 0.039 |
| Non-HDL | −16 (−7.0) | 0.007 | −21 (−11) | 0.008 |
| Triglycerides | −24 (−9.0) | NS | −35 (−27) | 0.039 |
| LDL/HDL | −0.3 (−7.0) | NS | −0.4 (−10) | 0.031 |
| PAI-1 | −4.0 (−20) | NS | −7.0 (−37) | 0.047 |

*P-values were computed using the log-normal distribution of the ratio of change from baseline to 12 weeks using the Wilcoxon Signed Rank test of the median. The Null Hypothesis assumed a mean change from baseline of zero.
NS = nonsignificant (P > 0.05)
†Subgroup of subjects selected with HbA1c greater than 5.4; bolding highlights subgroup differences.

In both groups, the effect of PC10 on oxLDL levels was significant. For the group overall, there was a 10% reduction that nearly placed subjects at completion in the low risk group. The subgroup began the trial at moderate risk and had improved with a fall to the low risk group by completion. This reduction in an important risk factor for the development of coronary artery disease offers an additional opportunity to promote healthy aging. The antioxidant components of the formula function to assist in lowering oxLDL levels and promote a healthy cholesterol metabolism to offer organ system protection.

Example 6

Synergistic Inhibition of Myeloperoxidase Activity by a Nine-Component Phytocomplex A trial was conducted to assess the ability of a 9-component phytocomplex (PC9p) to exhibit synergy in the in vitro inhibition of MPO. All Chemicals, Methods and Calculations were performed as described in Example 2.

PC9p Test Material—

The PC9p test material was formulated as a reduced version of PC10 lacking only the bergamont orange fruit extract (Table 8).

TABLE 8

Nine-component Phytocomplex (PC9)

| Test Material | Observed IC50 [µg/mL] | Relative Amount [F] |
|---|---|---|
| Apple fruit† | 3.86 (3.19-4.66) | 0.286 |
| Blueberry fruit* | 140 (92.4-212) | 0.048 |
| Capsicum fruit† | 34.5 (31.5-42.3) | 0.048 |
| Grape seed† | 2.40 (1.81-3.18) | 0.048 |
| Grape skin† | 34.5 (28.9-41.1) | 0.048 |
| Green tea leaf† | 0.883 (0.557-1.40) | 0.143 |
| Mangosteen pericarp† | 3.35 (2.46-4.56) | 0.048 |
| Olive leaf† | 8.82 (6.27-12.4) | 0.048 |
| Turmeric root & rhizome† | 95.5 (75.0-122) | 0.286 |

| | | Expected IC$_{50}$ [µg/mL] | Combination Index [Expected IC$_{50}$/Observed IC$_{50}$] |
|---|---|---|---|
| Phytocomplex (PC9) | 1.95* (1.19-4.03) | 3.68 | 1.89 |

†extract/
*concentrate/
** Phytocomplex PC9 contains relative amounts
*Observed IC50 of the PC9p formulation is significantly (p < 0.05) less than the Expected IC50 with a CI = 1.89 indicating synergy.

Conclusion—

The nine-component phytocomplex (PC9p) exhibited an unexpected increase 1.9-times the MPO-inhibitory activity of its individual components thus exhibiting synergy of the formulation (Table 8).

Example 7

Synergistic Inhibition of Myeloperoxidase Activity by Four-Component Phytocomplexes Two 4-component phytocomplexes, differing only in the ratios of their components were tested, to exhibit synergy in the in vitro inhibition of MPO. All Chemicals, Methods and Calculations were performed as described in Example 2.

PC9p Test Material—

The PC4x test combinations were formulated as a further reduced version of PC10 as described in Tables 9 and 10.

TABLE 9

CI of Four-Component Phytocomplex (PC4.1) for Myeloperoxidase Inhibition

| Test Material | Observed IC$_{50}$† [µg/mL] | Fraction of PC4.1 Formulation |
|---|---|---|
| Apple Fruit Extract | 3.86 (3.19-4.66) | 0.25 |
| Grape Seed Extract | 2.40 (1.81-3.18) | 0.25 |
| Green Tea Leaf Extract | 0.883 (0.557-1.40) | 0.25 |
| Olive Leaf Extract | 8.82 (6.27-12.4) | 0.25 |

TABLE 9-continued

CI of Four-Component Phytocomplex (PC4.1)
for Myeloperoxidase Inhibition

|  | Expected IC$_{50}$ [µg/mL] | Combination Index [Expected IC$_{50}$/ Observed IC$_{50}$] |  |
| --- | --- | --- | --- |
| PC4.2 | 1.08* (0.778-1.49) | 2.08 | 1.93 |

†Parenthetic values are 95% confidence interval.
*Observed IC50 significantly lower (p < 0.05) than the expected IC50 and CI = 1.93 indicating synergy of the four-component formulation.

The four-component phytocomplex (PC4.1) in the ratios of about 1:1:1:1 exhibited a dramatic, unexpected increase nearly 2-times the MPO-inhibitory activity of its individual components thus exhibiting synergy of the formulation (Table 9).

TABLE 10

CI of a Four-Component Phytocomplex (PC4.2)
for Myeloperoxidase Inhibition

| Test Material | Observed IC$_{50}$† [µg/mL] | Fraction of PC4.2 Formulation |
| --- | --- | --- |
| Apple Fruit Extract | 3.86 (3.19-4.66) | 0.55 |
| Grape Seed Extract | 2.40 (1.81-3.18) | 0.09 |
| Green Tea Leaf Extract | 0.883 (0.557-1.40) | 0.27 |
| Olive Leaf Extract | 8.82 (6.27-12.4) | 0.09 |

|  | Expected IC$_{50}$ [µg/mL] | Combination Index [Expected IC$_{50}$/ Observed IC$_{50}$] |  |
| --- | --- | --- | --- |
| PC4.2 | 0.42* (0.29-0.62) | 2.05 | 4.83 |

†Parenthetic values are 95% confidence interval.
*Observed IC50 significantly lower (p < 0.05) than the expected IC50 and CI = 4.83 indicating synergy of the four-component formulation.

The four-component phytocomplex (PC4.2) in the ratios of about 6:1:3:1 exhibited a dramatic, unexpected increase nearly 5-times the MPO-inhibitory activity of its individual components thus exhibiting synergy of the formulation (Table 10).

Example 8

Salivary Nitrite Levels after Oral Administration of Prototype and Commercial Nitric Oxide Generating Products in Healthy Volunteers Saliva nitrite production levels in healthy subjects were evaluated after taking commercial products containing putative NO generating actives. In the study, eight subjects between the ages of 18 to 72 performed a Berkeley Test® nitric oxide biomarker strip (NOBS) test early in the morning to determine their baseline level of salivary NO$_2$. If the baseline score was below 5 on the Visual scale, the subjects then proceeded to take one of the test articles listed in Table 11. After consumption of the test article, NOBS were developed at 30, 60, 90, 120 and 240 minutes.

TABLE 11

Description of the 15 Test Articles Used

| Test Article | Vendor | Product Code | Lot Number | Serving (g) |
| --- | --- | --- | --- | --- |
| ProArgi9 Purple Wave | Synergy | 72840 |  | 10.5 |
| ProArgi9 P1[a] | Synergy |  |  | 11.1 |
| Niteworks | Herbalife | 3150US | 475562B19 | 10.0 |
| BeetElite | Neogenis | NA | 17115 | 10.0 |
| NO3 Chrome[b] | Nutrabolt | 101742 | 0502C5 |  |
| L-Arginine Plus | Elements of Health Care LLC | LPLUS-01 | 151001 | 12.7 |
| L-Arginine Cardio Power | Nuvo Soma Labs | NA | U1510826 | 10.6 |
| Perfusia-SR | Thorne Research | LSA52508 | 316622 |  |
| L-Arginine Complete | Fenix Nutrition | 9015400288 | 47236300 | 10.0 |
| Arginine Infusion | Sante Global | NA | 15371 | 10.3 |
| Arginext[c] | High Desert Heart Inst. | NA | NA | 13.5 |
| Nitroxyl | Nitrosolution | XOOOMTPKU | 1502077 |  |
| LRG9 | NA | LRG912-BX30-V01 | 1420302 | 12.0 |
| Neo40 | Neogenis | NA | 142591S | 1.4 |
| Arginine Cardio[d] | Dr. Böger | 8104519792 | 15513 | 8 |

[a]ProArgi9 P1 contains FCC beet root powder (lot 45).
[b]1250 mg of arginine nitrate per serving (approximately 919 mg of arginine and 331 mg of nitrate based on molecular weight).
[c]Dr. Siva Arunasalam test article.
[d]Dr. Rainer Böger test article.

Berkeley Nitric Oxide Biomarker Strips (NOBS)—

NOBS were developed and immediately scored with Visual scoring card. Subjects with access to Argus app scored NOBS immediately. Subject (s) without access to Argus app submitted NOBS to the study monitor for scoring. Argus readings [units] were converted to µM Nitrite with an equation (y=0.0027x2+1.2755x+37.805; R2=0.9994) that described a 2nd degree polynomial relationship between Argus units and NOBS color development.

10 of the 15 test materials contained arginine or citrulline as a source of salivary NO$_2$, 4 contained only NO$_3$ as the source of salivary NO$_2$, and ProArgi9 P1 contained both the amino acids and red beet root as potential sources of salivary NO$_2$ (Table 12). The complete compositions of ProArgi9 Purple Wave and ProArgi9 P1 are presented in Tables 13 and 14, respectively.

Arginine/Citrulline Content of Test Materials—

Arginine or citrulline content of the test materials was obtained from labels on the commercial products. All commercial products were administered per serving instructions on the container.

Determination of Nitrate and Nitrite in Test Articles—

Nitrate/Nitrite (NOx) fluorometric assays were performed according to the manufacturer's instructions (Cayman Chemicals, Item No. 780051, Ann Arbor, Mich.). Results were tabulated as mg NOx/serving.

Pharmacokinetic Parameters and Calculations—

The pharmacokinetic parameter of area-under-the-curve (AUC) was computed using the trapezoidal method from 0 to 240 minutes. The extent of NO$_2$ increase relating to product administration was computed using the ratio of $AUC_{(0-240)}/eAUC$, where eAUC represented the endogenous salivaryNO2 and was computed using $C_0 \times 240$ min. Thus, $AUC_{(0-240)}/eAUC$ represented the systemic NO increase provided by the product. If the 95% Confidence Interval (CI) of the $AUC_{(0-240)}/eAUC$ included a value <1.0, it was assumed that the test material had no systemic impact on NO during the 240 minutes of the observation period.

TABLE 12

Arginine, Citrulline, Nitrate and Nitrite Content of the 15 Test Articles

| Test Article | Serving (g) | Arginine (g/serving) | Citrulline (g/serving) | Nitrate (mg/serving) | Nitrite (mg/serving) |
|---|---|---|---|---|---|
| ProArgi9 Purple Wave | 10.5 | 5.1 | 0.044 | <0.02 | <0.02 |
| ProArgi9 P1 | 11.1 | 5.1 | 0.005 | 76.7 | <0.02 |
| Niteworks | 10.0 | | 5.2[a] | <0.02 | <0.02 |
| BeetElite | 10.0 | | | 200 | 6.67 |
| NO3 Chrome | 2.10 | | | 307 | <0.03 |
| L-Arginine Plus | 12.7 | 5.1 | 1.01 | <0.03 | <0.03 |
| L-Arginine Cardio Power | 11.6 | 5.0 | 0.2 | <0.03 | <0.03 |
| Perfusia-SR | 1.39 | 1.0 | | <0.03 | <0.03 |
| L-Arginine Complete | 10.0 | 5.0 | 1.0 | <0.03 | <0.03 |
| Arginine Infusion | 10.3 | 5.0 | 1.0 | <0.03 | <0.03 |
| Arginext[d] | 13.5 | | 10.0[a] | <0.02 | <0.02 |
| Nitroxyl | 0.657 | | 0.25 | 1.21 | <0.03 |
| LRG9 | 12.0 | 5.0 | 1.0 | <0.03 | <0.03 |
| Neo40 | 1.4 | | | 1.49 | 9.10 |
| Arginine Cardio | 8.0 | | 7.58[a] | <0.02 | <0.02 |

[a]Proprietary blend of L-Arginine/L-Citrulline

TABLE 13

Composition of ProArg9 Purple Wave

| Ingredient | Amount (mg) |
|---|---|
| ProArgi-9 Plus Vitamin Base | 614 |
| Red Grape Polyphenol Extract [ExGrape(TM) red wine extract] | 50 |
| Grape Skin Extract/*Vitis vinifera* | 75 |
| Watermelon Whole Fruit Extract [20% Citrulline]/*Citrullus lanatus*, Watermelon Powdered Extract, 20% | 220.1 |
| Vitamin C (ascorbic acid) [100%, fine powder] | 75 |
| Vitamin B12 (cyanocobalamin) [1%, trituration] | 0.9 |
| Folic Acid [10%, trituration] | 3 |
| Vitamin B6 (pyridoxine hydrochloride) [82% B6] | 3 |
| Silicon Dioxide [Syloid ® 244] | 50 |
| D-Ribose | 100 |
| Vitamin D3 (cholecalciferol) [100,000 IU/g, 100 SD/S] | 37 |
| L-Arginine [granular] | 5100 |
| Pomegranate Fruit Juice Concentrate/*Punica granatum* | 500 |
| *Stevia* Leaf Extract/*Stevia rebaudiana* | 66 |
| Natural Citrus Sweetener [CitriSweet(TM)] | 430 |
| Xylitol [bulk] | 500 |
| Citric Acid | 2500 |
| Citrus Blend Natural Flavor [WONF] | 85 |
| Malic Acid | 500 |
| Huckleberry Natural Flavor | 85 |
| Silicon Dioxide [Syloid ® 244] | 120 |

TABLE 14

Composition of ProArgi9P1

| Ingredient | ProArgi9P1 (mg) |
|---|---|
| L-Arginine | 5100 |
| Citric Acid | 2000 |
| Red Beet Root | 2000 |
| Natural Citrus Sweetner | 430 |
| Malic Acid | 400 |
| Pomogrenate Fruit Juice Concentrate | 375 |

TABLE 14-continued

Composition of ProArgi9P1

| Ingredient | ProArgi9P1 (mg) |
|---|---|
| Silicon Dioxide | 170 |
| Thiamin (B1) (Thiamine mononitrate) | 110 |
| Calcium Ascorbate | 95 |
| Citrus Blend Natural Flavor | 85 |
| Huckleberry Natural Flavor | 85 |
| Magnesium Oxide | 84 |
| *Stevia* Leaf Extract* | 66 |
| Apple Fruit Extract | 30 |
| Watermelon Whole Fruit Extract | 23 |
| Vitamin D3 (Cholecalciferol) | 2.4 |
| Green Tea Leaf Extract | 15 |
| D-Ribose | 10 |
| Grape Skin Extract | 5.0 |
| Red Grape Polyphenol Extract | 5.0 |
| Grape Seed Extract | 5.0 |
| Olive Leaf Extract | 5.0 |
| Folic Acid | 3.0 |
| Vitamin B6 | 2.9 |
| Vitamin B12 | 0.345 |

TABLE 15

AUC and Relative Increases in AUC for the 11 Test Articles Containing Arginine or Citrulline

| Test Article | $AUC_{(0-24)}$[†] [mmol-min/L] | $AUC_{(0-24)}$[†] (95% CI) | AUC/ eAUC[††] | $AUC_{(0-24)}$/ eAUC (95% CI) |
|---|---|---|---|---|
| ProArgi9 Purple Wave | 25.9 | 20.3-33.2 | 1.23[a] | 1.03-1.47 |
| ProArgi9 P1 | 65.7 | 41.4-105 | 3.19[a] | 1.99-5.11 |
| Niteworks | 22.4 | 20.1-24.8 | 1.11 | 0.98-1.24 |
| L-Arginine Plus | 22.3 | 19.2-25.9 | 1.06 | 0.86-1.30 |
| L-Arginine Cardio Power | 21.1 | 19.6-22.7 | 1.00 | 0.92-1.10 |
| Perfusia | 22.9 | 20.9-25.2 | 0.96 | 0.77-1.19 |
| L-Arginine Complete | 21.1 | 19.7-22.7 | 1.07 | 0.98-1.17 |
| Arginine Infusion | 21.2 | 19.9-22.7 | 1.02 | 0.92-1.13 |
| Arginext | 22.0 | 20.0-24.2 | 1.03 | 0.99-1.07 |
| LRG9 | 24.4 | 18.8-31.8 | 1.14 | 0.92-1.42 |
| Arginine Cardio | 20.9 | 19.7-22.2 | 1.02 | 0.97-1.07 |

[†]Values are means of 8 independent observations; parenthetic values are 95% confidence limits
[††]The extent of NO2 increase relating to product administration was computed using the ratio of $AUC_{(0-240)}/eAUC$, where eAUC represented the endogenous salivary NO2 and was computed using $C_0 \times 240$ min. Thus, $AUC_{(0-240)}/eAUC$ represented the systemic NO increase provided by the product.
[a]Significant increase over endogenous NO2.

ProArgi9 P1 produced the greatest relative increase in salivary $NO_2$ with an $AUC_{(0-240)}/eAUC$ of 3.19 or a 3-fold increase in the endogenous level of $NO_2$. This effect was likely enhanced by the $NO_3$ content of ProArgi9P1 combined with MPO-inhibiting polyphenols. The only test material without $NO_3$ that produced a significant (P<0.05) increase over endogenous $NO_2$ was ProArgi9 Purple Wave, which demonstrated an enhanced systemic production of NO relative to formulations that do not contain WO-inhibiting polyphenols.

TABLE 16

AUC and Relative Increases in AUC for the 5 Test Articles Containing $NO_3$

| Test Article | $AUC_{(0-24)}$ [mmol-min/L] | $AUC_{(0-24)}$ (95% CI) | AUC/eAUC†† | AUC/eAUC (95% CI) |
|---|---|---|---|---|
| ProArgi9 P1 | 65.7 | 41.4-105 | 3.19[a] | 1.99-5.11 |
| BeetElite | 102 | 61.3-169 | 4.40[a] | 2.51-7.71 |
| NO3 Chrome | 107 | 60.5-189 | 5.00[a] | 2.84-8..80 |
| Nitroxyl | 20.2 | 19.4-21.1 | 1.00 | 0.94-1.06 |
| Neo40 | 24.3 | 20.6-28.6 | 1.14 | 0.96-1.35 |

† Values are means of 8 independent observations; parenthetic values are 95% confidence limits
††The extent of NO2 increase relating to product administration was computed using the ratio of $AUC_{(0-240)}$/eAUC, where eAUC represented the endogenous salivary NO2 and was computed using $C_0$ × 240 min. Thus, $AUC_{(0-240)}$/eAUC represented the systemic NO increase provided by the product.
[a]Significant increase over endogenous NO2.

Of the five test materials, only ProArgi9 P1, BeetElite and $NO_3$ Chrome produced significant (P<0.05) increases above endogenous $NO_2$ as represented by the lower limit of the 95% CI of the $AUC_{(0-240)}$/eAUC>1.0. The $NO_3$ content of these three products, however, varied greatly, 76.7, 200, and 307, respectively, for ProArgi9 P1, BeetElite, and $NO_3$ Chrome. To determine the effect of formulation on the increase in salivary $NO_2$, the AUC/eAUC ratio was adjusted for $NO_3$ dose (Table 17).

TABLE 17

NO3 Dose-adjusted Increases in AUC/eAUC for Test Materials Producing Salivary $NO_2$ Above Endogenous Levels

| Test Article | AUC/eAUC†# | (AUC/eAUC)/g NO3†† |
|---|---|---|
| ProArgi9 P1 | 3.19 | 42 (26-68)[a] |
| BeetElite | 4.40 | 22 (13-39)[b] |
| NO3 Chrome | 5.00 | 16 (9.3-29)[b] |

†Values are means of 8 independent observations.
The extent of NO2 increase relating to product administration was computed using the ratio of $AUC_{(0-240)}$/eAUC, where eAUC represented the endogenous salivary NO2 and was computed using $C_0$ × 240 min. Thus, $AUC_{(0-240)}$/eAUC represented the systemic NO increase provided by the product.
††Ratio adjusted for 76.7, 200 and 307 mg dosing respectively for ProArgi9 P1, BeetElite and NO3 Chrome; parenthetic value is 95% confidence interval.
[a,b]Uncommon superscripts indicate significant differences (P < 0.05).

When adjusted for $NO_3$ dose, the ProArgi9 P1 formulation was 1.9- and 2.6-fold more active than BeetElite and $NO_3$ Chrome, respectively. It can be inferred from this example that a formulation containing MPO-inhibiting polyphenols can enhance systemic production of NO from similar doses of $NO_3$ relative to formulations that do not contain MPO-inhibiting polyphenols.

Example 9

Formulations for Enhancing Nitric Oxide Production from Dietary $NO_3/NO_2$

Based upon results presented, the following formulations would be expected to perform as effectively as PA9-PW or ProArgi9P1.

TABLE 18

Composition of PA (NO+ (MY))

| Ingredient | (mg) |
|---|---|
| L-Arginine | 5100 |
| Citric Acid | 2200 |
| Red Beet Root (Nitrate 2%) | 2000 |
| Malic Acid | 450 |
| Natural Citrus Sweetener (CitriSweet ™) | 430 |
| Pomegranate Fruit Juice Concentrate | 375 |
| Silicon Dioxide (Syloid ® 244) | 170 |
| Thiamin (B1) (thiamie mononitrate) | 110 |
| Calcium Ascorbate (83% vit C, 9% Ca) | 95 |
| Citrus Blend Natural Flavor (WONF) | 90 |
| Natural Fresh Fruit Cherry | 90 |
| Magnesium Oxide (60% Mg, powder) | 84 |
| *Stevia* Leaf Extract | 66 |
| Apple Fruit Extract (75% polyphenols) | 30 |
| Watermelon Whole Fruit Extract (20% Citru | 23 |
| Green Tea Leaf Extract (80% decaffeinate) | 15 |
| D-Ribose | 10 |
| Grape Skin Extract | 5.0 |
| Red Grape Polyphenol Extract (ExGrape ™) | 5.0 |
| Grape Seed Extract (MegaNatural ®) | 5.0 |
| Olive Leaf Extract (12%, 7:1) | 5.0 |
| Folic Acid (10% trituration) | 3.0 |
| Vitamin B6 (pyridoxine hydrochloride) 82% | 2.9 |
| Vitamin D3 (cholecalciferol) (100,000 IU/g, | 2.4 |
| Vitamin B12 (cyanocobalamin) | 0.345 |

TABLE 19

Composition of ProArg9P2

| Ingredient | (mg) |
|---|---|
| L-Arginine | 5100 |
| Citric Acid | 2000 |
| Red Beet Root (about 2% NO3) | 2000 |
| Natural Citrus Sweetner | 430 |
| Malic Acid | 400 |
| Pomogrenate Fruit Juice Concentrate | 375 |
| Silicon Dioxide | 170 |
| Thiamin (B1) (Thiamine mononitrate) | 110 |
| Calcium Ascorbate | 95 |
| Citrus Blend Natural Flavor | 85 |
| Huckleberry Natural Flavor | 85 |
| Magnesium Oxide | 84 |
| *Stevia* Leaf Extract* | 66 |
| Apple Fruit Extract | 30 |
| Watermelon Whole Fruit Extract | 23 |
| Vitamin D3 (Cholecalciferol) | 2.4 |
| Green Tea Leaf Extract | 15 |
| D-Ribose | 10 |
| Grape Skin Extract | 5.0 |
| Red Grape Polyphenol Extract | 5.0 |
| Grape Seed Extract | 5.0 |
| Olive Leaf Extract | 5.0 |
| Folic Acid | 3.0 |
| Vitamin B6 | 2.9 |
| Vitamin B12 | 0.345 |

TABLE 20

Composition of Biome NO+

| Ingredient | (mg) |
|---|---|
| Red Grape Polyphenol Extract | 5.0 |
| Apple Fruit Extract [75% polyphenols]/*Malus pumila* | 30 |
| Grape Seed Extract [MegaNatural ®]/*Vitis vinifera* | 5.0 |
| Grape Skin Extract/*Vitis vinifera* | 40 |
| Green Tea Leaf Extract [80%, decaffeinated]/*Camellia sinensis* | 15 |
| L-Arginine [granular] | 1000 |
| Olive Leaf Extract [12%, 7:1]/*Olea europaea* | 5.0 |
| Pomegranate Fruit Juice Concentrate/*Punica granatum* | 450 |
| Red Beet Root (Nitrate 2%) (KR)/*Beta vulgaris* | 3000 |

TABLE 20-continued

Composition of Biome NO+

| Ingredient | (mg) |
| --- | --- |
| *Stevia* Leaf Extract/*Stevia rebaudiana* | 70 |
| Natural Citrus Sweetener [CitriSweet(TM)] | 450 |
| Watermelon Whole Fruit Extract [20% Citrulline]/*Citrullus lanatus* Watermelon Powdered Extract, 20% | 23 |
| Xylitol [bulk] | 500 |
| Vitamin C (ascorbic acid) [100%, fine powder] | 75 |
| Citric Acid | 1250 |
| Citrus Blend Natural Flavor [WONF] | 100 |
| Vitamin B12 (cyanocobalamin) [1%, trituration] | 0.9 |
| Folic Acid [10%, trituration] | 3.0 |
| L-Glutamine | 1000 |
| Inulin (chicory root extract) [HD food grade] | 2021 |
| Magnesium Oxide [60% Mg, powder] | 84 |
| Malic Acid | 275 |
| Natural Fresh Fruit Cherry | 89 |
| Vitamin B6 (pyridoxine hydrochloride) [82% B6] | 3.0 |
| Silicon Dioxide [Syloid ® 244] | 150 |
| Thiamin (B1) (thiamine mononitrate) [91% B1] | 110 |
| D-Ribose | 30 |
| Vitamin D3 (cholecalciferol) [100,000 IU/g, 100 SD/S] | 16 |

Methods for the production of these formulations and uses have been described. It will be readily apparent to those skilled in the art, however various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, powder, lotion, food, powder, or bar manufacturing process as well as vitamins, flavorings, and carriers. Other such changes or modifications would include the use of herbs or other botanical products containing the combinations of the preferred embodiments disclosed above. Many additional modifications and variations of the embodiments described herein may be made without departing from the scope, as is apparent to those skilled in the art. The specific embodiments described herein are offered by way of example only.

What is claimed is:

1. A composition for acutely raising nitric oxide levels in a subject, comprising:
   a) an effective amount of a nitric oxide synthase (NOS) dependent source of nitric oxide;
   b) an effective amount of a nitric oxide synthase NOS independent source of nitric oxide; and
   c) an effective amount of a myeloperoxidase inhibitor; wherein the composition acutely raises nitric oxide levels in a subject above a level provided by the available sources of nitric oxide in the subject prior to administration of the composition.

2. The composition of claim 1, wherein the level of nitric oxide in the subject following administration of the composition is greater than an amount provided by an equivalent amount of any one of the NOS dependent source of nitric oxide, the NOS independent source of nitric oxide, or the myeloperoxidase inhibitor.

3. The composition of claim 1, wherein the NOS dependent source of nitric oxide comprises from about 1 wt % to about 80 wt % of the composition.

4. The composition of claim 1, wherein the NOS dependent source of nitric oxide comprises a member selected from the group consisting of L-arginine, L-citrulline, ornithine, or a combination thereof.

5. The composition of claim 4, wherein a source of the L-citrulline comprises watermelon extract.

6. The composition of claim 1, wherein the NOS dependent source of nitric oxide comprises L-arginine and L-citrulline.

7. The composition of claim 6, wherein the L-arginine and L-citrulline are present in the composition at a weight percent concentration range from about 1:10 to about 10:1, respectively.

8. The composition of claim 1, wherein the NOS independent source of nitric oxide comprises beet root extract, vitamin B1, collard green extract, nut powders, spinach extract, broccoli extract, lettuce extract, celery, kale, watercress, carrot, arugula, mustard greens, or a combination thereof.

9. The composition of claim 8, wherein the NOS independent source of nitric oxide comprises beet root extract and vitamin B1.

10. The composition of claim 9, wherein the beet root extract comprises from about 5 wt % to about 90 wt % and wherein the vitamin B1 comprises from about 0.01 wt % to about 80 wt % of the composition.

11. The composition of claim 9, wherein the beet root extract and vitamin B1 are present in the composition at a weight percent concentration ratio ranging from about 50:1 to about 10:1, respectively.

12. The composition of claim 1, wherein the myeloperoxidase inhibitor comprises from about 1 wt % to about 90 wt %.

13. The composition of claim 1, wherein the myeloperoxidase inhibitor comprises pomegranate fruit extract, apple extract, blueberry extract, capsicum extract, green tea extract, olive extract, bergamot extract, mangosteen extract, or a combination thereof.

14. The composition of claim 13, wherein the myeloperoxidase inhibitor comprises apple extract, green tea extract, and olive extract.

15. The composition of claim 14, wherein the apple extract, green tea extract, and olive extract are present in the composition at a weight ratio of about 1:1:1.

16. The composition of claim 14, wherein the apple extract, green tea extract, and olive extract are present in the composition at a weight ratio of about 6:3:1.

17. The composition of claim 14, wherein the myeloperoxidase inhibitor further comprises pomegranate fruit extract.

18. The composition of claim 14, further comprising blueberry fruit extract, capsicum fruit extract, and turmeric root extract.

19. The composition of claim 18, wherein the blueberry fruit extract comprises from about 0.01 wt % to about 80 wt %, the capsicum fruit extract comprises from about 0.01 wt % to about 80 wt %, and the turmeric root extract comprises from about 0.01 wt % to about 80 wt % of the composition.

20. The composition of claim 18, wherein the apple extract, the green tea extract, the olive extract, the blueberry fruit extract, the capsicum fruit extract, and the turmeric root extract are present in the composition at a weight ratio of about 1:1:1:1:1:1.

21. The composition of claim 18, further comprising turmeric rhizome extract, and mangosteen extract.

22. The composition of claim 19, wherein the turmeric rhizome extract comprises from about 0.01 wt % to about 80 wt % and the mangosteen extract comprises from about 0.01 wt % to about 80 wt % of the composition.

23. The composition of claim 21, wherein the apple extract, the green tea extract, the olive extract, the blueberry fruit extract, the capsicum fruit extract, the turmeric root extract, the turmeric rhizome extract, and the mangosteen extract are present in the composition at a weight ratio of about 1:1:1:1:1:1:1:1.

24. The composition of claim 21, wherein the formulation further comprises bergamot fruit extract.

25. The composition of claim 24, wherein the apple extract, the green tea extract, the olive extract, the blueberry fruit extract, the capsicum fruit extract, the turmeric root extract, the turmeric rhizome extract, the mangosteen extract, and the bergamot fruit extract are present in the composition at a weight ratio of about 1:1:1:1:1:1:1:1:1.

26. The composition of claim 1, wherein the composition is an oral dosage formulation.

27. The composition of claim 26, wherein the oral dosage form comprises a capsule, a tablet, a powder, a beverage, a syrup, a suspension, or a food.

* * * * *